US009765328B2

(12) United States Patent
Chaput

(10) Patent No.: US 9,765,328 B2
(45) Date of Patent: Sep. 19, 2017

(54) NUCLEASE-RESISTANT DNA ANALOGUES

(71) Applicant: John Chaput, Phoenix, AZ (US)

(72) Inventor: John Chaput, Phoenix, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/950,946

(22) Filed: Nov. 24, 2015

(65) Prior Publication Data
US 2016/0145606 A1 May 26, 2016

Related U.S. Application Data

(60) Provisional application No. 62/084,089, filed on Nov. 25, 2014.

(51) Int. Cl.
C07H 21/00 (2006.01)
C12N 15/11 (2006.01)
C07H 1/00 (2006.01)

(52) U.S. Cl.
CPC ............ C12N 15/111 (2013.01); C07H 21/00 (2013.01); C07H 1/00 (2013.01); C12N 2310/32 (2013.01); C12N 2310/323 (2013.01); C12N 2320/51 (2013.01)

(58) Field of Classification Search
None
See application file for complete search history.

(56) References Cited

PUBLICATIONS

Yu et al. JACS (2013), vol. 135, pp. 3583-3591.*
Ellington et al., In Vitro selection of RNA molecules that bind specific ligands, Nature, Aug. 1990, 346(6287):818-822.
Tuerk et al., Systematic evolution of ligands by exponential enrichment: RNA ligands to bacteriophage T4 DNA polymerase, Science, Aug. 1990, 249(4968):505-510.
Robertson et al., Selection in vitro of an RNA enzyme that specifically cleaves single-stranded DNA, Nature, Mar. 1990, 344(6265):467-468.
Jenison et al., High-resolution molecular discrimination by RNA, Science, Mar. 1994, 263(5152):1425-1429.
Ekland et al., Structurally complex and highly active RNA ligases derived from random RNA sequences, Science, Jul. 1995, 269(5222):364-370.
Keefe et al., Aptamers as therapeutics, Nat Rev Drug Discov., Jul. 2010, 9(7):537-550.
Deleavey et al., Designing chemically modified oligonucleotides for targeted gene silencing, Chem Biol., Aug. 2012, 19(8):937-954.
Burnett et al., RNA-based therapeutics: current progress and future prospects, Chem Biol. Jan. 2012, 19(1):60-71.
Keefe et al., SELEX with modified nucleotides, Curr Opin Chem Biol., Aug. 2008, 12(4):448-456.
Lin et al., Modified RNA sequence pools for in vitro selection, Nucleic Acids Res., Dec. 1994, 22(24):5229-5234.
Ruckman et al., 2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain, J Biol Chem., Aug. 1998, 273(32)20556-20567.
Chaput et al., The emerging world of synthetic genetics, Chem Biol., Nov. 2012, 19(11):1360-1371.
Joyce, Evolution. Toward an alternative biology, Science, Apr. 2012, 336(6079):307-308.
Schoning et al., Chemical etiology of nucleic acid structure: the alpha-threofuranosyl-(3'→2') oligonucleotide system, Science, Nov. 2000, 290(5495):1347-1351.
Yang et al., Experimental evidence that GNA and TNA were not sequential polymers in the prebiotic evolution of RNA, J Mol Evol., Sep. 2007, 65(3):289-295.
Ebert et al., The structure of a TNA-TNA complex in solution: NMR study of the octamer duplex derived from alpha-(L)-threofuranosyl-(3'-2')-CGAATTCG, J Am Chem Soc., Nov. 2008, 130(45):15105-15115.
Wilds et al., Crystal structure of a B-form DNA duplex containing (L)-alpha-threofuranosyl (3'→2') nucleosides: a four-carbon sugar is easily accommodated into the backbone of DNA, J Am Chem Soc., Nov. 2002, 124(46):13716-13721.
Pallan et al., Why Does TNA Cross-Pair More Strongly with RNA Than with DNA? An Answer from X-ray Analysis, Angew. Chem. Int. Ed., Dec. 2003, 42(47):5893-5895.
Yu et al., Darwinian evolution of an alternative genetic system provides support for TNA as an RNA progenitor, Nat. Chem., Mar. 2012, 4(3):183-187.
Pinheiro et al., Synthetic genetic polymers capable of heredity and evolution, Science, Apr. 2012, 336(6079)341-344.
Yu et al., An efficient and faithful in vitro replication system for threose nucleic acid, J. Am. Chem. Soc., Mar. 2013, 135(9):3583-3591.
Trevino et al., Evolution of functional nucleic acids in the presence of nonheritable backbone heterogeneity, Proc Natl Acad Sci U S A., Aug. 2011, 108(33):13492-13497.
Zhang et al., Synthesis of threose nucleic acid (TNA) phosphoramidite monomers and oligonucleotide polymers, Curr Protoc Nucleic Acid Chem, Sep. 2012, 50:4.51.1-4.51.26.
Adamczyk et al., Synthesis of 5- and 6-hydroxymethylfluorescein phosphoramidites, J. Org. Chem., Jan. 2000, 65(2):596-601.
Kvach et al., 5(6)-Carboxyfluorescein Revisited: New Protecting Group, Separation of Isomers, and their Spectral Properties on Oligonucleotides, Bioconjugate Chem., Sep. 2007, 18(5):1691-1696.
Watts et al., Studies on the hydrolytic stability of 2'-fluoroarabinonucleic acid (2'F-ANA), Org. Biomol. Chem., 2009, 7(9)1904-1910.

(Continued)

Primary Examiner — Patrick Lewis
(74) Attorney, Agent, or Firm — Quarles & Brady LLP

(57) ABSTRACT

The present invention provides stable, nuclease-resistant TNA and TNA-DNA oligonucleotides, wherein the oligonucleotides are completely resistant to enzymatic degradation for at least 24-72 hours. Methods of synthesis and use in diagnostic and therapeutic applications are also provided. Specifically, in one embodiment, we describe the chemical and biological stability of TNA and mixed-backbone (mosaic) TNA-DNA oligonucleotides under a variety of conditions and sequence contexts.

12 Claims, 15 Drawing Sheets

(56) References Cited

PUBLICATIONS

Barrett et al., An in vivo evaluation of amphiphilic, biodegradable peptide copolymers as siRNA delivery agents, Int J Pharm., May 2014, 466(1-2):58-67.

Vinkenborg et al., Aptamers for allosteric regulation., Nat Chem Biol., Aug. 2011, 7(8):519-527.

Nimjee et al., Aptamers: an emerging class of therapeutics, Annu Rev Med., 2005, 56:555-583.

Bouchard et al., Discovery and development of therapeutic aptamers, Annu Rev Pharmacol Toxicol., 2010, 50:237-257.

Mayer, The chemical biology of aptamers, Angew Chem Int Ed, 2009, 48(15):2672-89.

Wilson et al., In Vitro Selection of Functional Nucleic Acids, Ann. Rev. Biochem., Jul. 1999, 68(1), 611-647.

Griffin et al., In vivo anticoagulant properties of a novel nucleotide-based thrombin inhibitor and demonstration of regional anticoagulation in extracorporeal circuits, Blood, Jun. 1993, 81(12):3271-3276.

Pagratis et al., Potent 2'-amino-, and 2'-fluoro-2'-deoxyribonucleotide RNA inhibitors of keratinocyte growth factor, Nat. Biotechnol., Jan. 1997, 15(1):68-73.

Freier et al., The ups and downs of nucleic acid duplex stability: Structure-stability studies on chemically-modified DNA:RNA duplexes, Nucleic Acids Res., 1997, 25(22):4429-4443.

Faria et al., Sugar boost: When ribose modifications improve oligonucleotide performance, Curr Opin Mol Ther, Apr. 2008, 10(2):168-175.

Ng et al., Pegaptanib, a targeted anti-VEGF aptamer for ocular vascular disease, Nat. Rev. Drug Discovery, Feb. 2006, 5(2):123-132.

Merki et al., Antisense Oligonucleotide Directed to Human Apolipoprotein B-100 Reduces Lipoprotein(a) Levels and Oxidized Phospholipids on Human Apolipoprotein B-100 Particles in Lipoprotein(a) Transgenic Mice, Circulation, Aug. 2008, 118(7):743-753.

Noronha et al., Synthesis and biophysical properties of arabinonucleic acids (ANA): Circular dichroic spectra, melting temperatures, and ribonuclease H susceptibility of ANA-RNA hybrid duplexes, Biochemistry, Jun. 2000, 39(24):7050-7062.

Cummins et al., Characterization of fully 2'-modified oligoribonucleotide hetero- and homoduplex hybridization and nuclease sensitivity, Nucleic Acids Res., Jun. 1995, 23(11):2019-2024.

Frieden et al., Nuclease Stability of LNA Oligonucleotides and LNA-DNA Chimeras, Nucleosides Nucleotides Nucleic Acids, Oct. 2003, 22(5):1041-1043.

* cited by examiner

FIG. 2A
tctctctctc*TTTTTTTT (SEQ ID NO:14)
↓ SVPE
tctctctctc (SEQ ID NO:1)
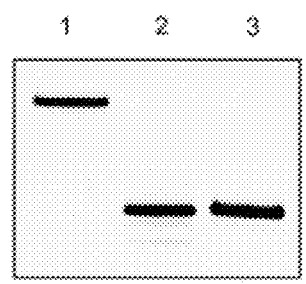
FIG. 2B
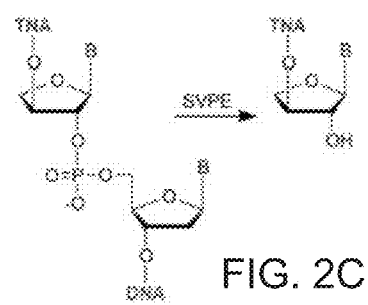
FIG. 2C

TNA Stability not Sequence Specific 2 nucleotide sequence
3'-AAA ACC CAC ACC ACC A-2'
(SEQ ID NO:16)
1  2  3

4 nucleotide sequence
3'-CAC TCG TAT GCA GTA G-2'
(SEQ ID NO:17)
1  2  3

1: buffer
2: human serum
3: human liver microsomes (7 days at 37° C)

SEQUENCE LISTING

```
<160> NUMBER OF SEQ ID NOS: 28

<210> SEQ ID NO 1
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(12)
<223> OTHER INFORMATION: alpha-(L)-threofuranosyl-(3'-2') nucleic acid
      TNA

<400> SEQUENCE: 1
tctctctctc tc                                                         12
```

-continued

```
<210> SEQ ID NO 2
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(7)
<223> OTHER INFORMATION: alpha-(L)-threofuranosyl-(3'-2') nucleic acid
      TNA
<220> FEATURE:
<221> NAME/KEY: modified_base
<222> LOCATION: (9)..(12)
<223> OTHER INFORMATION: alpha-(L)-threofuranosyl-(3'-2') nucleic acid
      TNA

<400> SEQUENCE: 2
tttttttctt tt                                                         12

<210> SEQ ID NO 3
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(5)
<223> OTHER INFORMATION: alpha-(L)-threofuranosyl-(3'-2') nucleic acid
      TNA
<220> FEATURE:
<221> NAME/KEY: modified_base
<222> LOCATION: (7)..(7)
<223> OTHER INFORMATION: alpha-(L)-threofuranosyl-(3'-2') nucleic acid
      TNA
<220> FEATURE:
<221> NAME/KEY: modified_base
<222> LOCATION: (9)..(12)
<223> OTHER INFORMATION: alpha-(L)-threofuranosyl-(3'-2') nucleic acid
      TNA

<400> SEQUENCE: 3
tttttctctt tt                                                         12

<210> SEQ ID NO 4
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(3)
<223> OTHER INFORMATION: alpha-(L)-threofuranosyl-(3'-2') nucleic acid
      TNA
<220> FEATURE:
<221> NAME/KEY: modified_base
<222> LOCATION: (5)..(5)
<223> OTHER INFORMATION: alpha-(L)-threofuranosyl-(3'-2') nucleic acid
      TNA
<220> FEATURE:
<221> NAME/KEY: modified_base
<222> LOCATION: (7)..(7)
<223> OTHER INFORMATION: alpha-(L)-threofuranosyl-(3'-2') nucleic acid
      TNA
<220> FEATURE:
<221> NAME/KEY: modified_base
<222> LOCATION: (9)..(9)
<223> OTHER INFORMATION: alpha-(L)-threofuranosyl-(3'-2') nucleic acid
      TNA
<220> FEATURE:
<221> NAME/KEY: modified_base
<222> LOCATION: (11)..(12)
```

-continued

<223> OTHER INFORMATION: alpha-(L)-threofuranosyl-(3'-2') nucleic acid
      TNA

<400> SEQUENCE: 4
tttctctctc tt                                                           12

<210> SEQ ID NO 5
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(1)
<223> OTHER INFORMATION: alpha-(L)-threofuranosyl-(3'-2') nucleic acid
      TNA
<220> FEATURE:
<221> NAME/KEY: modified_base
<222> LOCATION: (3)..(3)
<223> OTHER INFORMATION: alpha-(L)-threofuranosyl-(3'-2') nucleic acid
      TNA
<220> FEATURE:
<221> NAME/KEY: modified_base
<222> LOCATION: (5)..(5)
<223> OTHER INFORMATION: alpha-(L)-threofuranosyl-(3'-2') nucleic acid
      TNA
<220> FEATURE:
<221> NAME/KEY: modified_base
<222> LOCATION: (7)..(7)
<223> OTHER INFORMATION: alpha-(L)-threofuranosyl-(3'-2') nucleic acid
      TNA
<220> FEATURE:
<221> NAME/KEY: modified_base
<222> LOCATION: (9)..(9)
<223> OTHER INFORMATION: alpha-(L)-threofuranosyl-(3'-2') nucleic acid
      TNA
<220> FEATURE:
<221> NAME/KEY: modified_base
<222> LOCATION: (11)..(11)
<223> OTHER INFORMATION: alpha-(L)-threofuranosyl-(3'-2') nucleic acid
      TNA

<400> SEQUENCE: 5
tctctctctc tc                                                           12

<210> SEQ ID NO 6
<211> LENGTH: 12
<212> TYPE: DNA
<213> ORGANISM: Artificial Sequence
<220> FEATURE:
<223> OTHER INFORMATION: synthetic

<400> SEQUENCE: 6
cccccccccc cc                                                           12

<210> SEQ ID NO 7
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(6)
<223> OTHER INFORMATION: alpha-(L)-threofuranosyl-(3'-2') nucleic acid
      TNA
<220> FEATURE:
<221> NAME/KEY: modified_base
<222> LOCATION: (9)..(12)
<223> OTHER INFORMATION: alpha-(L)-threofuranosyl-(3'-2') nucleic acid
      TNA

```
<400> SEQUENCE: 7
tttttccctt tt                                                              12

<210> SEQ ID NO 8
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(5)
<223> OTHER INFORMATION: alpha-(L)-threofuranosyl-(3'-2') nucleic acid
      TNA
<220> FEATURE:
<221> NAME/KEY: modified_base
<222> LOCATION: (9)..(12)
<223> OTHER INFORMATION: alpha-(L)-threofuranosyl-(3'-2') nucleic acid
      TNA

<400> SEQUENCE: 8
tttttccctt tt                                                              12

<210> SEQ ID NO 9
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(4)
<223> OTHER INFORMATION: alpha-(L)-threofuranosyl-(3'-2') nucleic acid
      TNA
<220> FEATURE:
<221> NAME/KEY: modified_base
<222> LOCATION: (9)..(12)
<223> OTHER INFORMATION: alpha-(L)-threofuranosyl-(3'-2') nucleic acid
      TNA

<400> SEQUENCE: 9
ttttcccctt tt                                                              12

<210> SEQ ID NO 10
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(1)
<223> OTHER INFORMATION: alpha-(L)-threofuranosyl-(3'-2') nucleic acid
      TNA
<220> FEATURE:
<221> NAME/KEY: modified_base
<222> LOCATION: (3)..(3)
<223> OTHER INFORMATION: alpha-(L)-threofuranosyl-(3'-2') nucleic acid
      TNA
<220> FEATURE:
<221> NAME/KEY: modified_base
<222> LOCATION: (5)..(5)
<223> OTHER INFORMATION: alpha-(L)-threofuranosyl-(3'-2') nucleic acid
      TNA
<220> FEATURE:
<221> NAME/KEY: modified_base
<222> LOCATION: (7)..(7)
<223> OTHER INFORMATION: alpha-(L)-threofuranosyl-(3'-2') nucleic acid
      TNA
<220> FEATURE:
<221> NAME/KEY: modified_base
<222> LOCATION: (9)..(10)
<223> OTHER INFORMATION: alpha-(L)-threofuranosyl-(3'-2') nucleic acid
```

```
      TNA
<220> FEATURE:
<221> NAME/KEY: modified_base
<222> LOCATION: (12)..(12)
<223> OTHER INFORMATION: alpha-(L)-threofuranosyl-(3'-2') nucleic acid
      TNA

<400> SEQUENCE: 10
tctctctctt ct                                                        12

<210> SEQ ID NO 11
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(16)
<223> OTHER INFORMATION: alpha-(L)-threofuranosyl-(3'-2') nucleic acid
      TNA

<400> SEQUENCE: 11
tttttttttt tttttt                                                    16

<210> SEQ ID NO 12
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(16)
<223> OTHER INFORMATION: alpha-(L)-threofuranosyl-(3'-2') nucleic acid
      TNA

<400> SEQUENCE: 12
aaaatttatt tattaa                                                    16

<210> SEQ ID NO 13
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(16)
<223> OTHER INFORMATION: alpha-(L)-threofuranosyl-(3'-2') nucleic acid
      TNA

<400> SEQUENCE: 13
ttaataaata aatttt                                                    16

<210> SEQ ID NO 14
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(12)
<223> OTHER INFORMATION: alpha-(L)-threofuranosyl-(3'-2') nucleic acid
      TNA

<400> SEQUENCE: 14
tctctctctc tcttttttttt                                               20
```

```
<210> SEQ ID NO 15
<211> LENGTH: 12
<212> TYPE: RNA
<213> ORGANISM: Artificial Sequence
<220> FEATURE:
<223> OTHER INFORMATION: synthetic

<400> SEQUENCE: 15
ucucucucuc uc                                                             12

<210> SEQ ID NO 16
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(16)
<223> OTHER INFORMATION: alpha-(L)-threofuranosyl-(3'-2') nucleic acid
      TNA

<400> SEQUENCE: 16
aaaacccaca ccacca                                                         16

<210> SEQ ID NO 17
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(16)
<223> OTHER INFORMATION: alpha-(L)-threofuranosyl-(3'-2') nucleic acid
      TNA

<400> SEQUENCE: 17
cactcgtatg cagtag                                                         16

<210> SEQ ID NO 18
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(3)
<223> OTHER INFORMATION: alpha-(L)-threofuranosyl-(3'-2') nucleic acid
      TNA
<220> FEATURE:
<221> NAME/KEY: modified_base
<222> LOCATION: (5)..(5)
<223> OTHER INFORMATION: alpha-(L)-threofuranosyl-(3'-2') nucleic acid
      TNA
<220> FEATURE:
<221> NAME/KEY: modified_base
<222> LOCATION: (7)..(7)
<223> OTHER INFORMATION: alpha-(L)-threofuranosyl-(3'-2') nucleic acid
      TNA
<220> FEATURE:
<221> NAME/KEY: modified_base
<222> LOCATION: (9)..(12)
<223> OTHER INFORMATION: alpha-(L)-threofuranosyl-(3'-2') nucleic acid
      TNA

<400> SEQUENCE: 18
tttctctctt tt                                                             12
```

```
<210> SEQ ID NO 19
<211> LENGTH: 16
<212> TYPE: DNA
<213> ORGANISM: Artificial Sequence
<220> FEATURE:
<223> OTHER INFORMATION: synthetic

<400> SEQUENCE: 19
aaaacccaca ccacca                                                      16

<210> SEQ ID NO 20
<211> LENGTH: 16
<212> TYPE: DNA
<213> ORGANISM: Artificial Sequence
<220> FEATURE:
<223> OTHER INFORMATION: synthetic

<400> SEQUENCE: 20
tggtggtgtg ggtttt                                                      16

<210> SEQ ID NO 21
<211> LENGTH: 16
<212> TYPE: RNA
<213> ORGANISM: Artificial Sequence
<220> FEATURE:
<223> OTHER INFORMATION: synthetic

<400> SEQUENCE: 21
aaaacccaca ccacca                                                      16

<210> SEQ ID NO 22
<211> LENGTH: 16
<212> TYPE: RNA
<213> ORGANISM: Artificial Sequence
<220> FEATURE:
<223> OTHER INFORMATION: synthetic

<400> SEQUENCE: 22
uggugguguu uuuuuu                                                      16

<210> SEQ ID NO 23
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(16)
<223> OTHER INFORMATION: 2'-fluoro-arabino nucleic acid FANA

<400> SEQUENCE: 23
aaaacccaca ccacca                                                      16

<210> SEQ ID NO 24
<211> LENGTH: 16
<212> TYPE: RNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(16)
<223> OTHER INFORMATION: 2'-fluoro-RNA

<400> SEQUENCE: 24
aaaacccaca ccacca                                                      16
```

```
<210> SEQ ID NO 25
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(20)
<223> OTHER INFORMATION: 2'-fluoro-RNA

<400> SEQUENCE: 25
gacactcgta tgcagtagcc                                           20

<210> SEQ ID NO 26
<211> LENGTH: 16
<212> TYPE: RNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(16)
<223> OTHER INFORMATION: 2'-methoxy-RNA

<400> SEQUENCE: 26
aaaacccaca ccacca                                               16

<210> SEQ ID NO 27
<211> LENGTH: 17
<212> TYPE: RNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(17)
<223> OTHER INFORMATION: 2'-methoxy-RNA

<400> SEQUENCE: 27
ggaccggaag guacgag                                              17

<210> SEQ ID NO 28
<211> LENGTH: 16
<212> TYPE: RNA
<213> ORGANISM: Artificial Sequence
<220> FEATURE:
<223> OTHER INFORMATION: synthetic

<400> SEQUENCE: 28
ugguggugug gguuuu                                               16
```

NUCLEASE-RESISTANT DNA ANALOGUES

CROSS-REFERENCE TO RELATED APPLICATIONS

This application claims the benefit of U.S. provisional Application No. 62/084,089 filed Nov. 25, 2014 entitled "Nuclease-Resistant DNA Analogues," which is incorporated by reference herein in its entirety.

STATEMENT REGARDING FEDERALLY SPONSORED RESEARCH

This invention was made with government support under CHM 1304583 awarded by the National Science Foundation. The government has certain rights in the invention.

BACKGROUND OF THE INVENTION

For more than 20 years, laboratories around the world have applied the principles of Darwinian evolution to isolate nucleic acid molecules with ligand binding affinity and catalytic activity[1-3]. DNA and RNA molecules isolated from these selections have been shown to distinguish closely related analogues by a difference of more than 10,000-fold in binding affinity and can accelerate the rate of a chemical reaction by as much as 1010 fold over the uncatalyzed reaction rate[4,5]. However, despite their ability to fold into shapes with desired functional properties, natural genetic polymers are poor candidates for many diagnostic and therapeutic applications due to their rapid degradation by nucleases[6].

This problem can be overcome by removing endogenous DNA- and RNA-degrading enzymes from the sample prior to analysis, but this strategy does not work if the target is a protein or a protein-bound cofactor. Similarly, if the genetic polymers are intended for therapeutic use in vivo, endogenous nucleases will be present in the blood and other biological fluids and tissues that will degrade DNA and RNA before they reach their target. Consequently, numerous chemical modifications have been developed that stabilize the nucleic acid backbone against nuclease digestion[7,8]. Substitution of the 2'-hydroxyl position of RNA with a methoxy (2'-OMe) or fluoro (2'-F) group, for example, provides resistance against enzymes that utilize the 2' position to attack the phosphodiester bond. However, care should be taken when modifying oligonucleotides, as chemical changes can adversely affect the functional properties of in vitro selected sequences[9].

A more direct approach for advancing functional nucleic acid molecules in the clinic is to develop in vitro selection systems that can be used to evolve synthetic genetic polymers with nuclease-resistant backbones. This approach is desirable, because it avoids the time consuming process of nuclease depletion and sequence re-engineering.

While early work in this area focused on the use of subtle modifications that were tolerated by natural polymerases[10,11], new advances in polymerase engineering have made it possible to synthesize unnatural genetic polymers with diverse backbone structures[12]. These molecules have been termed xeno nucleic acids (or XNA), because they are foreign to biological systems[13].

TNA ($\alpha$-(L)-threofuranosyl-(3'-2') nucleic acid) is a synthetic genetic polymer in which the natural three-carbon ribose sugar found in RNA is replaced with an unnatural fourcarbon tetrofuranose $\alpha$-(L) threose sugar. TNA polymers have phosphodiester linkages that occur between the 3' and 2' carbon positions, which leads to a backbone repeat unit that is one atom shorter than the backbone unit found in DNA and RNA. However, despite this difference, TNA is able to form stable anti-parallel Watson-Crick duplex structures with complementary strands of DNA RNA, and TNA[14,15]. The NMR structure of a self-complementary TNA duplex reveals a helical geometry that is similar to A-form RNA, which explains the ability for TNA to crosspair with DNA and RNA[16]. The crystal structure of a TNA modified strand indicates that threose prefers a C4'-exo conformation with a rigid backbone and a quasi trans-diaxial orientation of the 3' and 2' substituents that allows for DNA and RNA crosspairing by maximizing the spacing between adjacent nucleotides[17,18].

Using in vitro selection, we have previously isolated a TNA aptamer that can bind to human thrombin with high affinity and specificity[19]. Similar results were also obtained for hexose nucleic acid (HNA), in which HNA aptamers were evolved to bind the HIV trans5 activating response RNA element and the protein hen egg lysozyme[20]. While these aptamers represent the first examples of functional XNA molecules isolated by in vitro selection, growing interest in the field of synthetic genetics suggests that many different types of XNA molecules will be developed in the near future[12]. As XNA technology continues to advance, it has become important to assess the chemical and biological stability of XNA polymers in environments where these molecules are expected to function.

In their original study, Eschenmoser and colleagues demonstrated that TNA is stable for 8 days at pH 8[14]. To better understand the constraints of TNA polymers, we evaluated the chemical and biological stability of TNA and mixed-backbone (mosaic) TNA-DNA oligonucleotides under a variety of conditions and sequence contexts[22].

Accordingly, a need exists for stable, nuclease-resistant oligonucleotides for use in diagnostic and therapeutic applications.

SUMMARY OF THE INVENTION

In the present invention, we provide stable, nuclease-resistant TNA oligonucleotides comprising an effective amount of TNA, wherein the TNA oligonucleotide is completely resistant to enzymatic degradation for at least 72 hours. Methods of synthesis and use in diagnostic and therapeutic applications are also provided.

In the present invention, we provide stable, nuclease-resistant TNA-DNA oligonucleotides comprising an effective amount of TNA, wherein the TNA-DNA oligonucleotide is completely resistant to enzymatic degradation for at least 24 hours. Methods of synthesis and use in diagnostic and therapeutic applications are also provided.

In one embodiment, we describe the chemical and biological stability of TNA and mixed-backbone (mosaic) TNA-DNA oligonucleotides under a variety of conditions and sequence contexts. We find that TNA remains undigested after 3 days in simulated gastric fluid at 37° C., but degrades with a half-life of ~6 hours when incubated in an alkaline solution of 1 M NaOH at 65° C. TNA is completely stable against all nucleases tested, including an in vitro animal model designed to assess TNA stability in vivo.

In addition, we also find that mixed-backbone TNA-DNA oligonucleotides are resistant to enzymatic degradation by RNAse A, RQ1 DNAse, and Turbo DNAse, while mung bean nuclease and snake venom phosphodiesterase degrade internal DNA residues with varying degrees of efficiency.

These findings make TNA one of the most nuclease-resistant nucleic acid analogues developed to date.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2A: Synthetic strategy showing the chimeric TNA-DNA oligonucleotide before and after digestion with snake venom phosphodiesterase (SVPE). TNA lower case blue letters. DNA upper case red letters.

FIG. 2B: Analysis of the reaction products by polyacrylamide gel electrophoresis. Lanes 1 and 2: Fam-labeled (tc)6-dT8 before and after treatment with SVPE, respectively. Lane 3: size matched TNA-DNA hybrid 3'-tttCtCtCtt-2' (SEQ ID NO: 4).

FIG. 2C: Cleavage product of (tc)6-dT8 verified by ESI-TOF mass spectrometry.

DETAILED DESCRIPTION OF THE INVENTION

I. In General

Figure 1A:
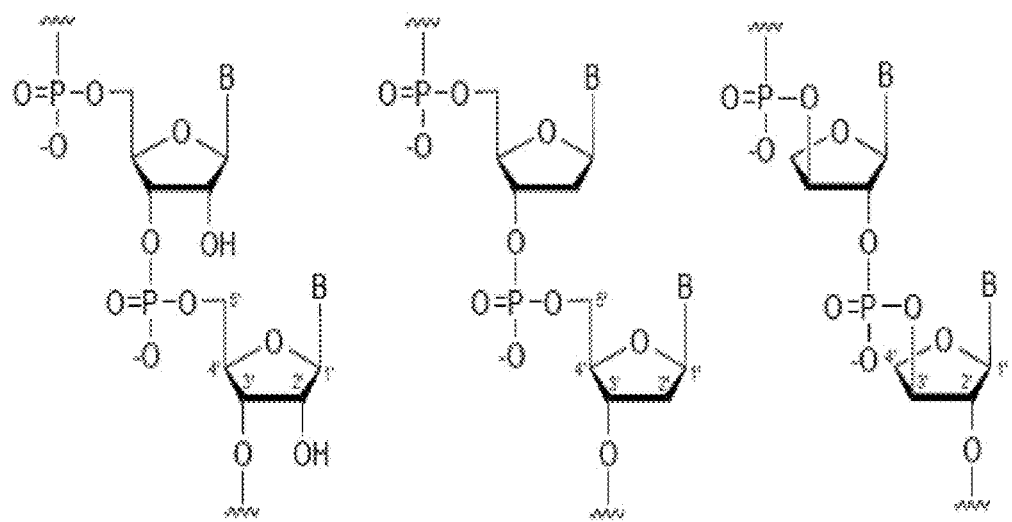
FIG. 1A: Constitutional structures of RNA, DNA and TNA.

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

In one embodiment, the invention provides stable, nuclease-resistant TNA oligonucleotides, wherein the TNA oligonucleotides comprise an effective amount of TNA and is completely resistant to enzymatic degradation. By "effective amount" we mean an amount of TNA sufficient to yield the sufficient resistance to enzymatic degradation. In one embodiment, the effective amount of TNA may comprise at least one TNA nucleic acid. In another embodiment, the effective amount of TNA may comprise at least two TNA nucleic acids. In other embodiments, the effective amount of TNA may comprise at least four TNA nucleic acids, at least five TNA nucleic acids, at least six TNA nucleic acids, at least seven TNA nucleic acids, at least ten nucleic acids.

By "resistant to enzymatic degradation" we mean the TNA oligonucleotide of the present invention resists degradation by enzymes including, without limitation, snake venom phosphodiesterase, RNAse A, RQ1 DNAse, and Turbo DNAse, for at least 72 hours.

In one embodiment, the invention provides stable, nuclease-resistant TNA-DNA oligonucleotides, wherein the TNA-DNA oligonucleotides comprise an effective amount of TNA and is resistant to enzymatic degradation. By "effective amount" we mean an amount of TNA sufficient to yield the sufficient resistance to enzymatic degradation. In one embodiment, the effective amount of TNA may comprise at least one TNA nucleic acid. By "resistant to enzymatic degradation" we mean the TNA-DNA oligonucleotide of the present invention resists degradation by enzymes including, without limitation, RNAse A, RQ1 DNAse, and Turbo DNAse, for at least 24 hours.

In another embodiment, the invention provides a method of preparing nuclease-resistant TNA-DNA oligonucleotides, the method comprising inserting an effective amount of TNA into a sample of DNA to yield a TNA-DNA oligonucleotide, wherein the TNA-DNA oligonucleotide is resistant to enzymatic degradation.

In some embodiments, the effective amount of TNA in a TNA-DNA oligonucleotide is at least one TNA. In some embodiments, the effective amount of TNA in a TNA-DNA oligonucleotide is at least two TNA, at least three TNA, at least four TNA, at least 5 TNA, at least 6 TNA, at least 7 TNA, at least 8 TNA, at least 9 TNA, at least 10 TNA, at least 15 TNA, at least 20 TNA, at least 25 TNA, at least 30 TNA, and may contain any number of TNA inbetween.

In some embodiments, the effective amount of TNA in a TNA-DNA oligonucleotide is at least 1% of the oligomers, at least 2% of the oligomers, at least 5%, or at least 7% of the oligomers. In some embodiments, the effective amount of TNA in the TNA-DNA oligonucleotide is at least 10% of the oligomers, at least 15% of the oligomers, at least 20% of the oligomers, at least 25% of the oligomers, at least 30% of the oligomers, at least 35% of the oligomers, at least 40% of the oligomers, at least 50% of the oligomers, at least 60% of the oligomers, at least 70% of the oligomers, at least 80% of the oligomers and any amounts or ranges inbetween (for example, 6%, 7%, 8%, 9%, 11%, 12%, 13%, 14%, 15%, 17%, 18%, 19%, 21%, 22%, 23%, 24%, 26%, 26%, 27%, 28%, 29%, 31%, 32%, 33%, 42%, 55%, 58%, 66% etc. etc.).

In another embodiment, the invention provides methods of using the nuclease-resistant TNA and TNA-DNA oligonucleotides of the present invention. The nuclease-resistant TNA and TNA-DNA oligonucleotides of the present invention may be used as a therapeutic (antisense, catalyst, RNAi etc), affinity reagent (aptamer, ribozyme) for diagnostic drug delivery, diagnostic testing, imaging etc. Basically, the nuclease-resistant TNA and TNA-DNA oligonucleotides of the present invention may be substituted in part or in whole for any application that currently uses DNA or RNA.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

III. Examples

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Experimental; General

All chemicals and reagents were purchased from commercial sources unless otherwise noted. Anhydrous CH2Cl2, EtOAc, DMF were obtained from Sigma-Aldrich or Acros Organics. SVPE refers to Phosphodiesterase I from *Crotalus adamanteus* venom obtained from Sigma-Aldrich. 5(6)-carboxy-fluorescein was obtained from Novabiochem®. All 1H NMR and 13C NMR spectra were obtained from 400 MHz Varian liquid-state NMR. The spin multiplicities are indicated by the symbols s (singlet), d (doublet), dd (doublet of doublets), t (triplet), q (quartet), m (multiplet), br (broad) and coupling constants (J) reported in hertz (Hz). Thin layer chromatography (TLC) was performed on glass-backed silica TLC plates. Column chromatography was performed on silica gel (40-63 μM). The mass spectra were obtained on Applied Biosytems Voyager System 4320 MALDI-TOF in positive polarity at Arizona State University and Xevo G2-S Q-TOF (Waters) equipped with ESI source and time of flight analyzer, coupled with Waters Acquity UPLC system at Michigan State University Mass Spectrometry and Metabolics Core facility.

3',6-Bis-pivaloyl-5(6)-carboxyfluorescein (2)

To a cooled (0-5° C.) solution containing 5(6)-carboxyfluorescein (1) (3.76 g, 9.72 mmol) in anhydrous DMF (24 mL) was added N,N-diisoprolylethylamine (DIEA) (6.76 mL, 5.0 g, 38.8 mmol) followed by trimethylacetic anhydride (4.34 mL, 3.98 g, 21.4 mmol). The mixture was stirred under argon at room temperature in the dark for 72 h. TLC (CH2Cl2-MeOH 25:1) showed the reaction to be complete. The solvent was removed under diminished pressure to afford a brown syrup. The residue was dissolved in EtOAc (60 mL) and CH2Cl2 (30 mL) and washed with three 60-mL portions of 1 M phosphate buffer (pH 7) and 60 mL of brine. The organic layer was dried over MgSO4 and evaporated under diminished pressure to give compound 2 as yellow foam. The residue was dried under high vacuum overnight and used directly in the following reaction; 1H NMR (400 MHz, CDCl3) δ 8.76 (s, 1H, 5-isomer), 8.36 (dd, 2H, J=8.8 Hz and 12 Hz), 8.14-8.12 (d, 1H, J=7.6, 6-isomer), 7.87 (s, 1H, 6-isomer), 7.28 (d, 1H, J=8.0 Hz, 5-isomer), 7.08 (m, 4H), 6.83-6.76 (m, 8H), 1.35 (s, 36H, tBu); 13C NMR (100 MHz, CDCl3) δ 176.48 (5), 176.44 (6), 169.07 (6), 168.86 (5), 168.08 (6), 167.98 (5), 157.47 (5), 153.19 (6), 152.79 (5), 152.76 (6), 151.53 (6), 151.44 (5), 136.70 (5), 135.87 (6), 131.75 (6), 131.63 (5), 130.02 (6), 128.67 (5, 6), 127.59 (5), 126.61 (5), 125.85 (6), 125.46 (6), 124.44 (5), 117.89 (5), 117.85 (6), 115.39 (6), 115.31 (5), 110.49 (5), 110.47

(6), 82.15 (6), 81.93 (5), 39.18 (5, 6), 27.02 (5, 6); mass spectrum (MALDI) m/z 545.5 (M+H)+ (C31H28O9 requires 545.2).

3',6-Bis-pivaloyl-6-carboxyfluorescein pentafluorophenyl ester (3)

To a cooled (0-5° C.) solution containing compound 2 in 75 mL of EtOAc was added a solution of pentafluorophenol (2.14 g, 11.6 mmol) in EtOAc (10 mL) followed by a solution of N,N'-dicyclohexylcarbodiimide (2.40 g, 11.6 mmol) in EtOAc (30 mL) over 80 min. After stirring for 2 h at 0-5° C., the cooling bath was removed and the mixture was stirred at r.t. for 18 h. The precipitated dicyclohexylurea was filtered and the filtrate evaporated under diminished pressure. The residue was purified on a silica gel column eluting with hexanes-EtOAc 9:1 to obtain 5-carboxy ester (2.28 g, 32%) and 6-carboxy ester 3 (1.85 g, 26%) as white foams; 1H NMR (400 MHz, CDCl3) δ 8.45 (dd, 1H, J=1.2 Hz and 7.6 Hz), 8.21 (d, 1H, J=8.4 Hz), 7.96 (s, 1H), 7.10 (s, 2H), 6.86-6.83 (m, 4H), 1.37 (s, 18H); mass spectrum (MALDI) m/z 711.4 (M+H)+ (C37H27F5O9 requires 711.1).

3',6-Bis-pivaloyl-6-(6-hydroxyhexylaminocarbonyl)-fluorescein (4).

To a solution containing 3 (500 mg, 0.70 mmol) in CH2Cl2 (5 mL) was added (134 μL, 0.77 mmol) of DIEA followed by a solution of 6-aminohexanol (90 mg, 0.77 mmol) in CH2Cl2 (1 mL). The mixture was stirred at r.t. under argon for 3 h then diluted with CH2Cl2 (25 mL). The organic phase was washed with water (20 mL), satd. aq. NaHCO3 (20 mL), brine (25 mL), dried over MgSO4 and evaporated under diminished pressure. The crude residue was purified on a silica gel column eluting with CH2Cl2-EtOAc 3:2 to afford compound 4 (378 mg, 83%) as colorless foam; 1H NMR (400 MHz, DMSO-d6) δ8.67-8.45 (t, 1H, J=5.6 Hz), 8.18 (dd, 2H, J=8.0 Hz and 24 Hz), 7.77 (s, 1H), 7.29 (s, 2H), 6.96-6.91 (m, 4H), 4.28 (t, 2H, J=5.2 Hz), 3.35 (t, 2H, J=6.0 Hz), 3.18 (dd, 2H, J=6.4 Hz), 1.45 (t, 2H, J=6.8 Hz), 1.31 (s, 18H), 1.36 (t, 2H, J=6.4 Hz); 13C NMR (100 MHz, DMSO-d6): δ 176.40, 168.23, 164.60, 152.89, 152.81, 151.27, 141.71, 130.30, 129.82, 127.81, 125.77, 122.63, 118.99, 116.17, 110.79, 110.00, 81.62, 61.04, 32.84, 29.38, 27.11, 26.82, 25.63; mass spectrum (MALDI) m/z 666.5 (M+Na)+ (C37H41NNaO9 requires 666.3).

Phosphoramidite.

In a dry flask containing 4 (50 mg, 77.6 μmol), anhydrous acetonitrile was added to obtain a 0.1M solution followed by 2-cyanoethyl N,N,N',N'-tetraisopropyl phosphoramidite (25 μL, 77.6 μmol). The mixture was stirred for 5 min upon which 1-H tetrazole (207 μL, 93 μmol, 0.45 M solution in acetonitrile) was added and the mixture stirred for 30 min. The reaction mixture was filtered through a 0.45-μm disposable syringe filter into clean and dry bottle under inert atmosphere. The phosphoramidite bottle was placed on the amidite port of the DNA synthesizer and used immediately for synthesis. The coupling of Fam phosphoramidite with terminal hydroxyl of oligonucleotides was conducted using 5-(ethylthio)-1H-tetrazole.

Oligonucleotide Synthesis.

Oligonucleotide synthesis and 6-fluorescein aminohexanol phosphoramidite (FAM) labeling was performed using an automated ABI 3400 DNA synthesizer in trityl-off mode on a 1 μmol scale. The oligonucleotides were deprotected from the solid support in concentrated NH4OH for 18 h at 55° C., precipitated in n-butanol, and purified by polyacrylamide gel electrophoresis (PAGE). Oligonucleotide concentrations were determined by optical density at a wavelength of 260 nm using known DNA and RNA extinction coefficients. The identity of oligonucleotides was confirmed by MALDI-TOF and ESI-TOF mass spectrometry. Gel imaging of FAM-labeled oligonucleotides was performed on Ambersham Biosciences Typhoon TRIO+ Variable Mode Imager using laser excitation at 532 nm and 526 nm short-pass emission filter for fluorescein.

Preparation of TNA Oligonucleotide 1.

Synthesis of 3'-FAM-tctctctctctcTTTTTTTT-3' (SEQ ID NO:14) was performed on an automated ABI 3400 DNA synthesizer in trityl-off mode on 1 μM scale following a protocol described previously. The oligonucleotide was deprotected from solid support in concentrated NH4OH for 18 h at 55° C., precipitated in n-butanol and purified by 20% denaturing PAGE and electroeluted. The DNA portion of the strand was removed by nuclease digestion wherein 280 μg (100 μL) of 3'-FAM-tctctctctctcTTTTTTTT-3' (SEQ ID NO:14) was taken in 495 μL of reaction buffer (Tris-Borate 50 mM, MgCl2 7 mM, pH 7.5) followed by addition of 55 μL of SVPE (55 mU) to give a final volume of 650 μL. The reaction mixture was incubated for 24 h at 37° C. and the product was PAGE purified. The identity of the oligonucleotide was confirmed by ESI-TOF mass spectrometry (Table 2).

Chemical Stability Assay.

Pepsin-free simulated gastric fluid (SGF) was prepared by autoclaving a solution of NaCl (200 mg) in nanopure water (99 mL) followed by addition of 6N HCl (0.7 mL, pH 1.25). TNA (30 pmol), DNA (45 pmol), and RNA (5 pmol) were added to SGF (20 μL) and incubated for the specified time (up to 72 hours). Following the incubation, the reaction mixture was neutralized by the addition of 1N NaOH and the solutions were stored at −20° C. until the time course was complete. The volume was then reduced to 10 μL, mixed with 10 μL of loading buffer (8 M Urea, 5 mM Tris.HCl, 20 mM EDTA, pH 7.5), and the oligonucleotides were analyzed by denaturing PAGE and imaged. The same protocol was used to monitor alkaline stability.

Nuclease Stability Assay.

The FAM labeled TNA, DNA and chimeric DNA-TNA oligonucleotides (30-45 pmol) were incubated for 24 h at 37° C. in presence of RNase A, RQ1 DNase, Turbo™ DNase, Mung Bean Nuclease and phosphodiesterase I from *Crotalus adamanteus* venom using the manufacture recommended protocol and buffer. After 24 hours, the reaction mixture was quenched by the addition of stop buffer (8 M Urea, 5 mM Tris.HCl, 20 mM EDTA, pH 7.5) and the reaction was analyzed by PAGE. Reaction buffers: RNase A [50 mM NaOAc (pH 5.0) and 2.5 μg/μL RNase A in a volume of 10 μL]; RQ1 DNase Assay [40 mM Tris-HCl, 10 mM MgSO4, 1 mM CaCl2, pH 8.0] and 0.1 U/μL of RQ1 DNase in a volume of 10 μL]; Turbo™ DNase 1× Turbo DNAse reaction buffer and 0.2 U/μL of Turbo™ DNase in a volume of 10 μL; mung bean nuclease [NaCl 30 mM, NaOAc 50 mM, ZnSO4 1 mM, pH 5] and 1 U/μL of mung bean nuclease in a volume of 10 μL; and snake venom phosphodiesterase [Tris-Borate 50 mM, MgCl2 7 mM, pH 7.5] and 100 μU/μL of SVPE in a volume of 10 μL.

In Vitro Animal Model.

Rat liver lysosomal lysate was prepared from 8 week old mixed gender Sprague Dawley rats using a modified protocol based on published methods27. The protocol was developed at Merck and transferred to XenoTech, LLC (Lenexa, Kans.) such that lysosomal lysate can be obtained as a custom product (CPH-12-054). Lysosomal lysates were diluted with 20 mM sodium citrate buffer (pH 5.0) to a concentration of 0.4 mg/mL of protein (0.5 units/mL of acid phosphatase activity) and then incubated with 1 μM TNA or siRNA (diluted from a 100 μM stock solution) at 37° C. in a 5% CO2 incubator for up to 24 h. Similarly, mouse serum (from Bioreclamation; pool of 100+ female CD-1 mice) was incubated with 1 μM TNA or siRNA (diluted from a 100 μM stock solution) at 37° C. in a 5% CO2 incubator for up to 24 h. At specified time points, a 100 μL aliquot was quenched with an equal volume of Phenomenex Clarity Load Lysis buffer (version 2.0) containing 1 μM internal standard (a truncated single stranded siRNA). Phenomenex Clarity OTX solid phase extraction (SPE) 96-well plates were used to clean up the TNA and siRNA samples according to the manufacturer's guidelines except that equilibration and wash buffers contained ammonium acetate instead of sodium phosphate. Following elution from SPE plates, organic solvent was removed using a steady stream of nitrogen for 1 h and samples were lyophilized overnight. Dried samples were reconstituted in 300 μL of RNase-free water containing 1 mM EDTA prior to injection of samples (10 μL) onto an LC-MS system consisting of an HTC PAL autosampler, a Michrom Paradigm MS4 HPLC pump, and a Thermo Exactive orbitrap mass spectrometer utilizing an ESI source and operated in negative ion mode. Separation was performed with a Waters Xbridge OST C18 column (2.5 μm, 2.1×50 mm) at a temperature of 75° C. using a flow rate of 250 μL/min and a gradient of 1.7 mM triethylamine (TEA) and 100 mM hexafluoroisopropanol (HFIP) in water (solvent A) and 90/10 (v/v) acetonitrile/methanol (solvent B) as follows: initiate at 5% B and hold to 1 min, ramp to 40% B at 3.5 min, ramp to 90% B at 3.6 min, hold at 90% B until 5 min, ramp down to 5% B at 5.1 min, and hold at 5% B until end of run at 7 min. Data processing of high resolution mass spectra (including peak finding, charge deconvolution, and deisotoping) as well as parent siRNA and metabolite identification were performed using ProMass HR software (Novatia) in conjunction with Thermo Xcalibur software. The intensity ratios of parent to internal standard were calculated and converted to percentage of parent oligonucleotide remaining by setting the t=0 ratio value as 100%.

Chemical Synthesis.

Figure 1B:
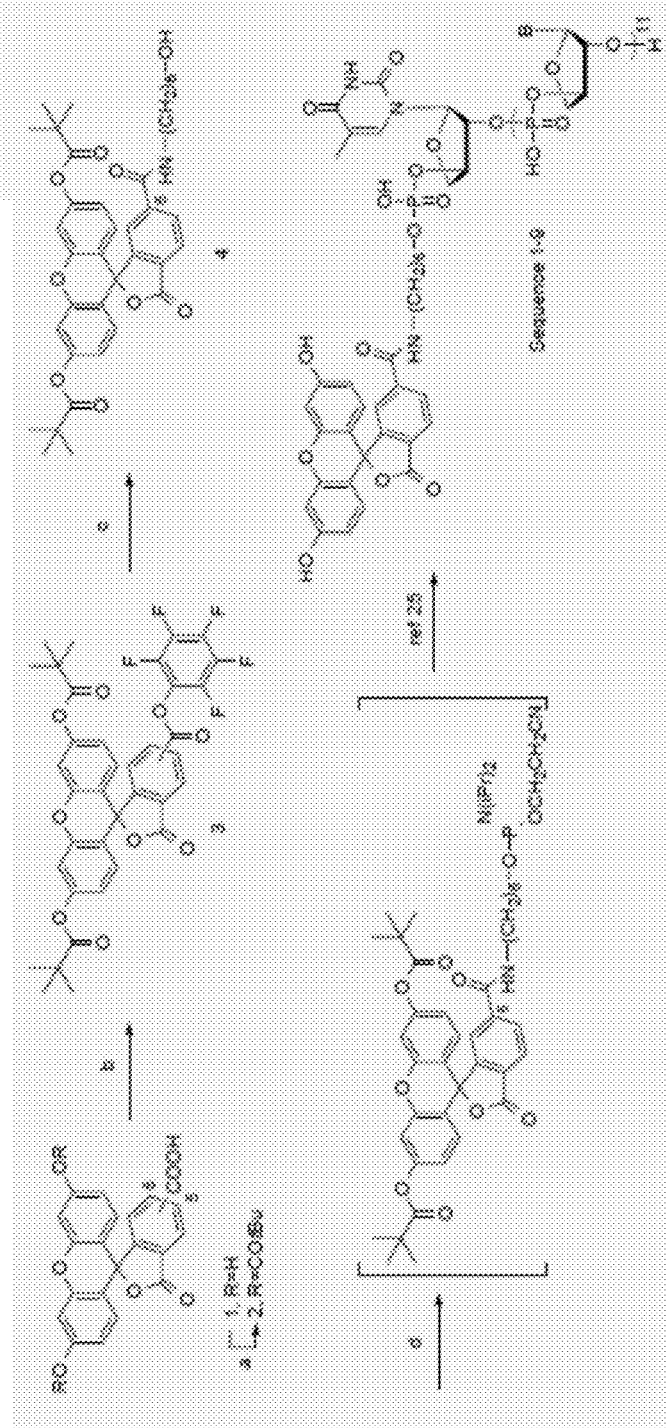
FIG. 1B: Chemical synthesis of 6-carboxyfluorescein phosphoramidite.

We began by chemically synthesizing the α-L-threofurosyl nucleoside phosphoramidites required to construct TNA polymers by solid-phase synthesis on an automated DNA synthesizer[23]. In addition, we also synthesized 6-carboxyfluorescein phosphoramidite (FIG. 1B) to label TNA oligonucleotides with a fluorescent tag. This last step was necessary, because TNA is not recognized by standard intercalating agents like ethidium bromide and Sybr Gold that are commonly used to stain DNA and RNA, and TNA is not a substrate for T4 polynucleotide kinase.

Starting from a mixture of 5(6)-carboxyfluorescein 1, the 3' and 6' hydroxyl groups were esterified with pivaloyl anhydride to give the pivalate diester derivative 2 as an inseparable mixture of both 5- and 6-carboxy regioisomers[24]. For reasons of instability, the pivalate diester derivative 2 was converted to the pentafluorophenyl ester 3, which allowed us to obtain the 6-pentafluorophenyl regioisomer 3 after purification[25]. Subsequent reaction of pentafluorophenyl ester 3 with 6-aminohexanol afforded amide 4, which was phosphitylated and used in situ for TNA labeling on the DNA synthesizer[25].

The TNA- and mixed-backbone TNA-DNA oligonucleotides were prepared by solidphase synthesis using two different strategies. This was necessary since a TNA-derivatized CPG column was not available when the oligonucleotides were synthesized. The all-TNA strand (3'-tctctctctctc-2' (SEQ ID NO: 1)) was synthesized as a longer TNA-DNA chimera (3'-tctctctctctc-2'-5'-TTTTTTTT-3' (SEQ ID NO: 14)), where lower case residues are TNA and upper case residues are DNA) using a DNA CPG column. The synthetic oligonucleotide was then deprotected with concentrated NH4OH and treated with snake venom phosphodiesterase (SVPE) to remove the DNA tail (FIG. 2). Analysis of the SVPE treated product by denaturing polyacrylamide gel electrophoresis revealed a single band that migrated with the same electrophoretic mobility as a size-matched TNA/DNA hybrid (3'-tttCtCtCtCtt-2' (SEQ ID NO: 4)). Mass spectrometry confirmed that SVPE treatment produced the desired TNA molecule with a free 2' hydroxyl group, indicating that cleavage occurred between the 2' hydroxyl and 5' phosphate moieties of the 2'-5' TNA-DNA junction.

Figure 5:
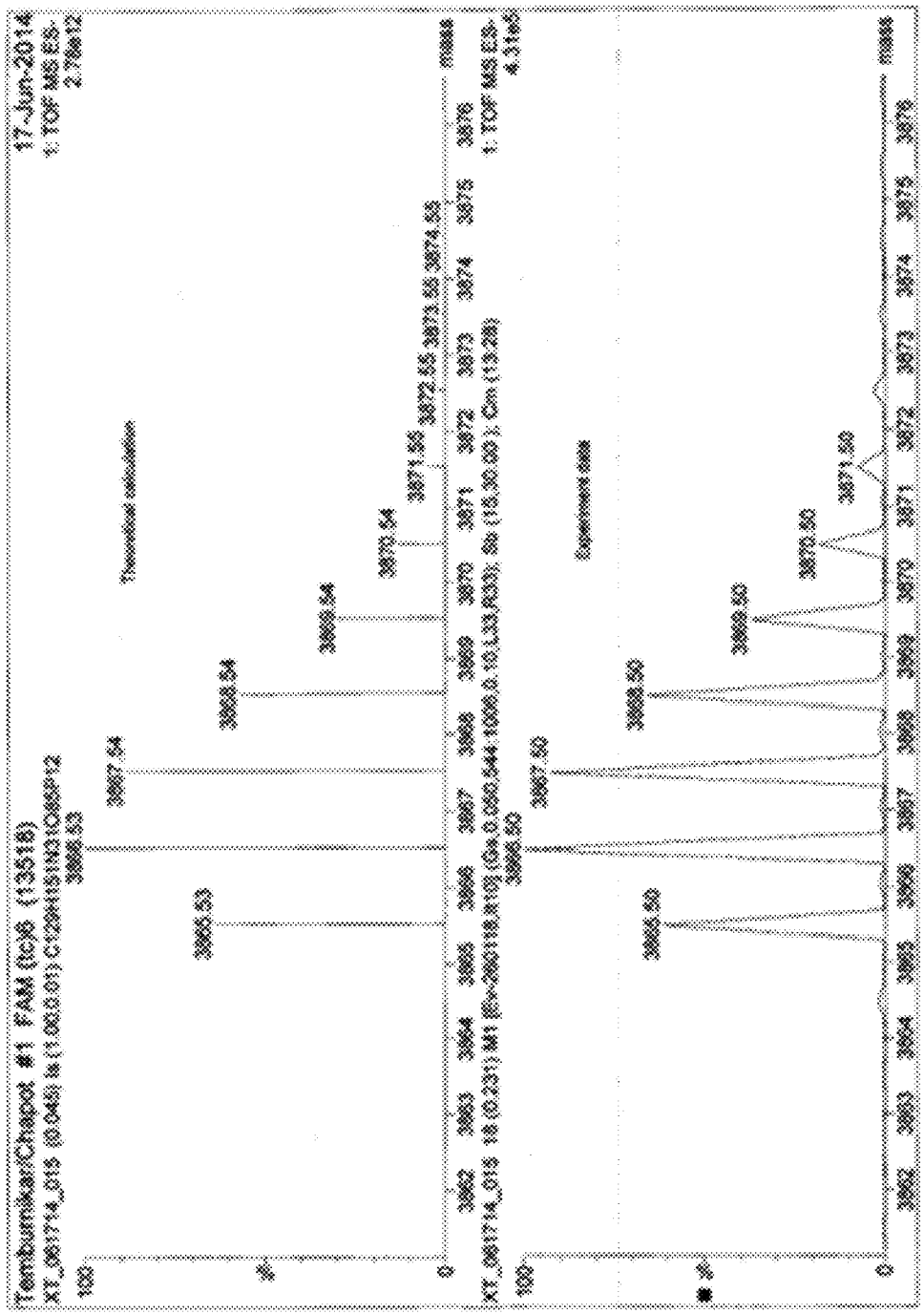
FIG. 5. Mass Spectroscopic analysis of oligonucleotide obtained upon Snake Venom Phosphodiesterase digested Fam-labeled $(tc)_6$-$dT_8$.

Treatment of the size-matched TNA/DNA hybrid with SVPE produced as series of shorter truncated products (FIG. 2), indicating that internal DNA residues are not protected from digestion by SPVE. Since the susceptibility of the desired product to SVPE prevents the use of the TNA-DNA chimera approach, the remaining mixed backbone TNA-DNA sequences (Table 1) were prepared using a universal solid support column. This approach produced a series of higher mass products due to branching on the solid support column. Nevertheless, we were able to obtain sufficient quantities of the alternating and consecutive mosaic TNA-DNA strands after purification by gel electrophoresis. Each strand was verified by mass spectrometry to confirm that the correct TNA oligonucleotides were obtained (FIG. 5, Table 2). In the future, we will use solid support columns that are derivatized with TNA monomers. These columns have since been prepared and shown to function with high efficiency (data not shown).

TABLE 1

TNA and mixed-backbone TNA-DNA oligonucleotides.[a,b]

| SEQ ID NO: | Alternating | SEQ ID NO: | Consecutive |
|---|---|---|---|
| 1 | 3'-tctctctctctc-2' | 1 | 3'-tctctctctctc-2' |
| 2 | 3'-tttttttCtttt-2' | 2 | 3'-tttttttCtttt-2' |
| 3 | 3'-tttttCtCtttt-2" | 7 | 3'-ttttttCCtttt-2' |
| 4 | 3'-tttCtCtCtCtt-2' | 8 | 3'-tttttCCCtttt-2' |
| 5 | 3'-tCtCtCtCtCtC-2' | 9 | 3'-ttttCCCCtttt-2' |
| 6 | 5-CCCCCCCCCCCC-3' | 6 | 5-CCCCCCCCCCCC-3' |

[a]DNA residues are given as upper case letters.
[b]TNA residues are given as lower case letters.

TABLE 2

Mass Spectrometry analysis of TNA oligonucleotides.

| Sequence No. | Sequence | Calculated [M+] | Observed* |
|---|---|---|---|
| 1 | 3'-FAM-tctctctctctc-2' | 3865.52 | 3866.50 |
| 2 | 3'-FAM-tttttttCtttt-2' | 3954.54 | 3957.52 |
| 3 | 3'-FAM-tttttCtCtttt-2' | 3953.55 | 3956.34 |

TABLE 2-continued

Mass Spectrometry analysis of TNA oligonucleotides.

| Sequence No. | Sequence | Calculated [M⁺] | Observed* |
|---|---|---|---|
| 4 | 3'-FAM-tttCtCtCtCtt-2' | 3951.59 | 3952.60 |
| 10 | 3'-FAM-tCtCtCtCttCt-2' | 3949.62 | 3951.88 |
| 6 | 5'-FAM-CCCCCCCCCCCC-3' | 3943.71 | 3945.26 |
| 7 | 3'-FAM-tttttCCtttt-2' | 3953.55 | 3955.90 |
| 8 | 3'-FAM-ttttCCCtttt-2' | 3952.57 | 3953.60 |
| 9 | 3'-FAM-tttCCCCtttt-2' | 3951.59 | 3954.33 |
| 11 | 3'-tttttttttttttttt-2' | 4578.53 | 4580.50 |
| 12 | 3'-aaaatttatttattaa-2' | 4550.52 | 4651.60 |
| 13 | 3'-ttaataaataaatttt-2' | 4650.62 | 4651.60 |

Chemical Stability.

Figure 3:
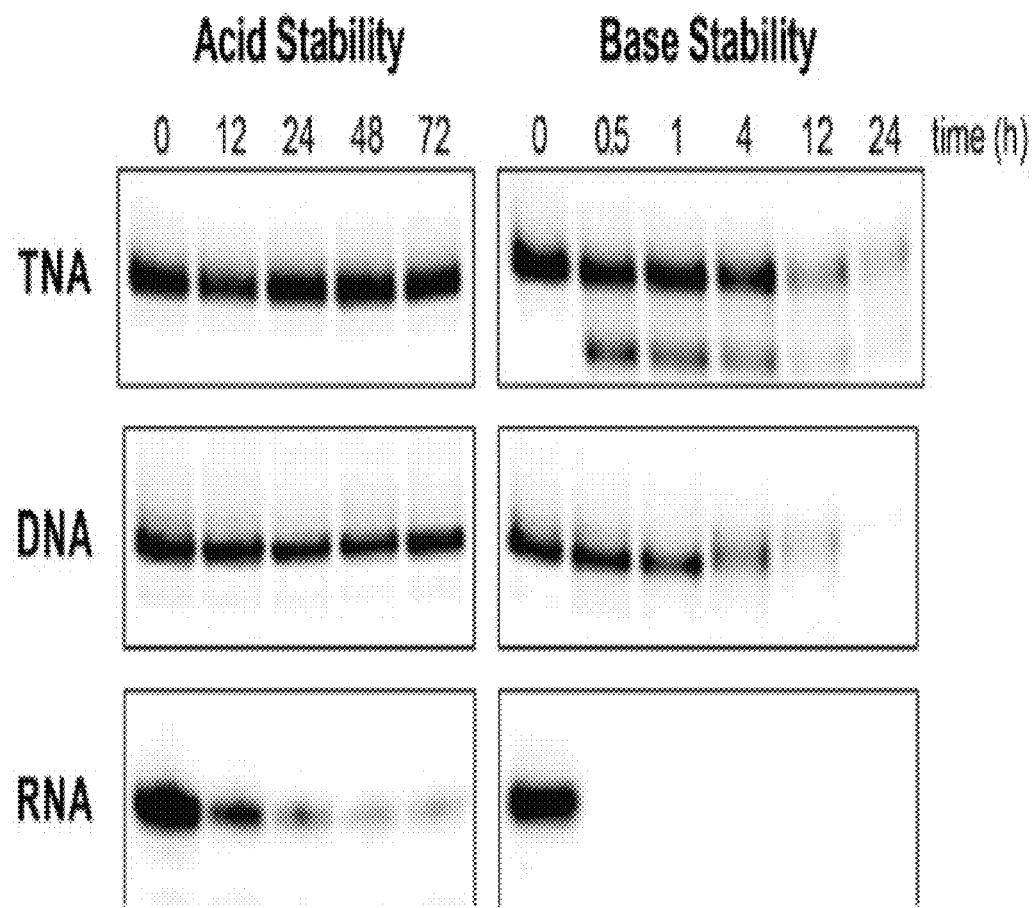
FIG. 3: Chemical stability of TNA, DNA, and RNA oligonucleotides under extreme acidic and alkaline conditions. Oligonucleotide stability was evaluated under acid conditions that simulate the gastric environment (pH 1.2 at 37° C.) and alkaline conditions (1M NaOH at 65° C.). Strand stability was monitored by denaturing polyacrylamide gel electrophoresis. Strand sequences: TNA (3'-Fam-tctctctctctc-2' (SEQ ID NO:1)); DNA (5'-Fam-CCCCCCCCCCCC-3') (SEQ ID NO:6); and RNA (5'-32P-UCUCUCUCUCUC-3' (SEQ ID NO: 15)).
Figure 6:
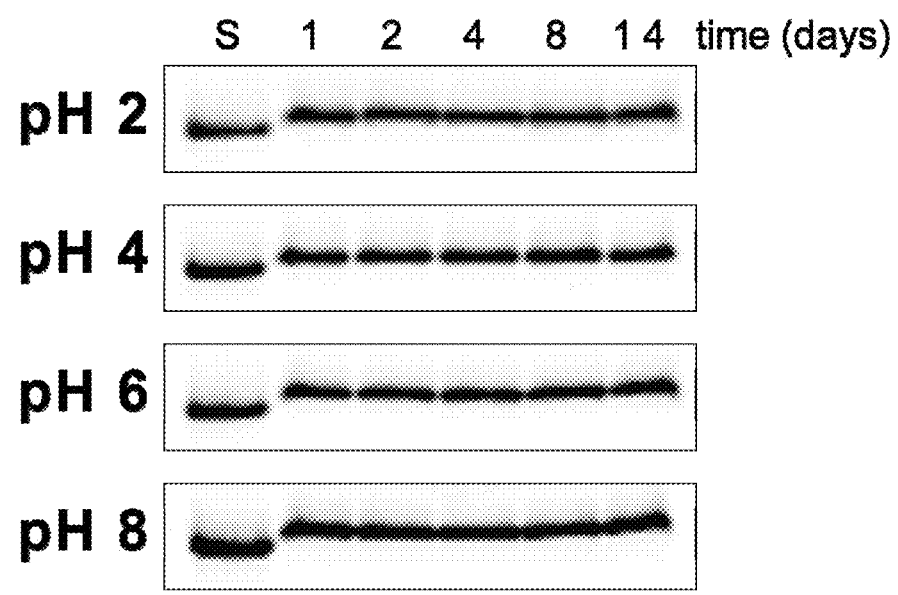
FIG. 6. Chemical stability of TNA oligonucleotide (3'-Fam-tctctctctctc-2' (SEQ ID NO:1)) under pH conditions. Oligonucleotide stability was evaluated in presence of 1 M NaCl, 0.25 M $MgCl_2$, 0.1 M HEPES buffer, pH adjusted to 2, 4, 6, and 8 at 25° C. for days 1, 2, 4, 8 and 14. TNA oligonucleotide strand stability was monitored by denaturing polyacrylamide gel electrophoresis. Band S, TNA (3'-Fam-tctctctctctc-2' (SEQ ID NO:1)) in stop buffer (8M Urea, 5 mM Tris.HCl, 20 mM EDTA), Band 1-14 TNA strand incubated in buffer with pH 2, 4, 6 and 8.
Figure 7:
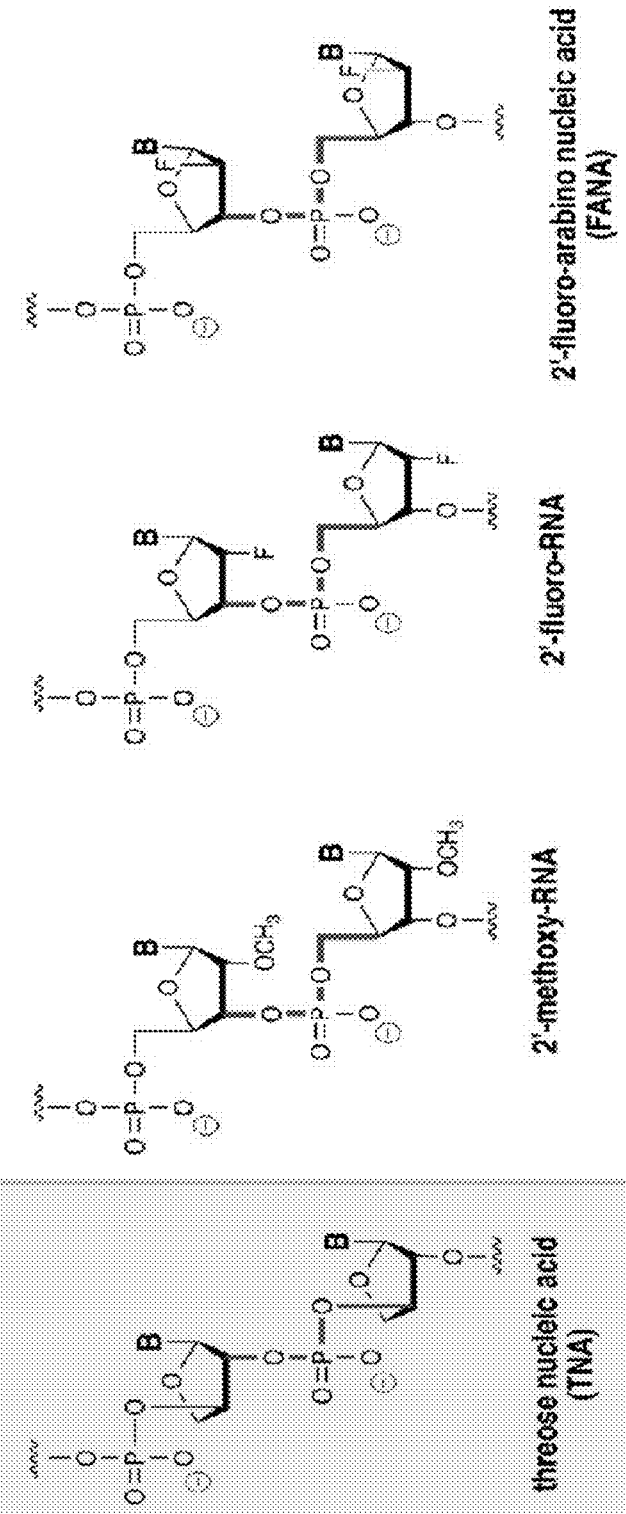
FIG. 7 is a cartoon depiction of Threose nucleic acid (TNA), 2'-methyoxy-RNA, 2'-fluoro-RNA, and 2'-fluoro-arabino nucleic acid (FANA).

We compared the chemical stability of the all-TNA strand to DNA and RNA oligonucleotides of identical length and similar sequence. An initial screen of pH conditions revealed that the TNA strand remained intact after 14 days at 25° C. when incubated in buffered solutions ranging from pH 2 to pH 8 (FIG. 6). Based on this result, we chose more extreme conditions to study the chemical stability of TNA. For these experiments, pepsin-free simulated gastric fluid (SGF, pH 1.25) and 1 M NaOH were used to maintain parity with previous antisense studies[26]. For the acidic regime, the TNA, DNA, and RNA samples were incubated in SGF for 72 hours at 37° C. Under these conditions, 85% of the RNA sample degraded in the first 12 hours, while the DNA and TNA samples remained intact after 72 hours (FIG. 3). For the alkaline regime, the TNA, DNA, and RNA samples were incubated in 1 M NaOH for 24 hours at 65° C. Under these conditions, the RNA sample is degraded within the first 30 minutes, while trace amounts of the DNA and TNA samples are still visible after 12 and 24 hours, respectively (FIG. 3). We estimate based on their time-dependent degradation pattern that DNA and TNA have half-lives of approximately 1.5 and 6 hours, respectively, under these conditions.

Nuclease Stability.

Figure 4:
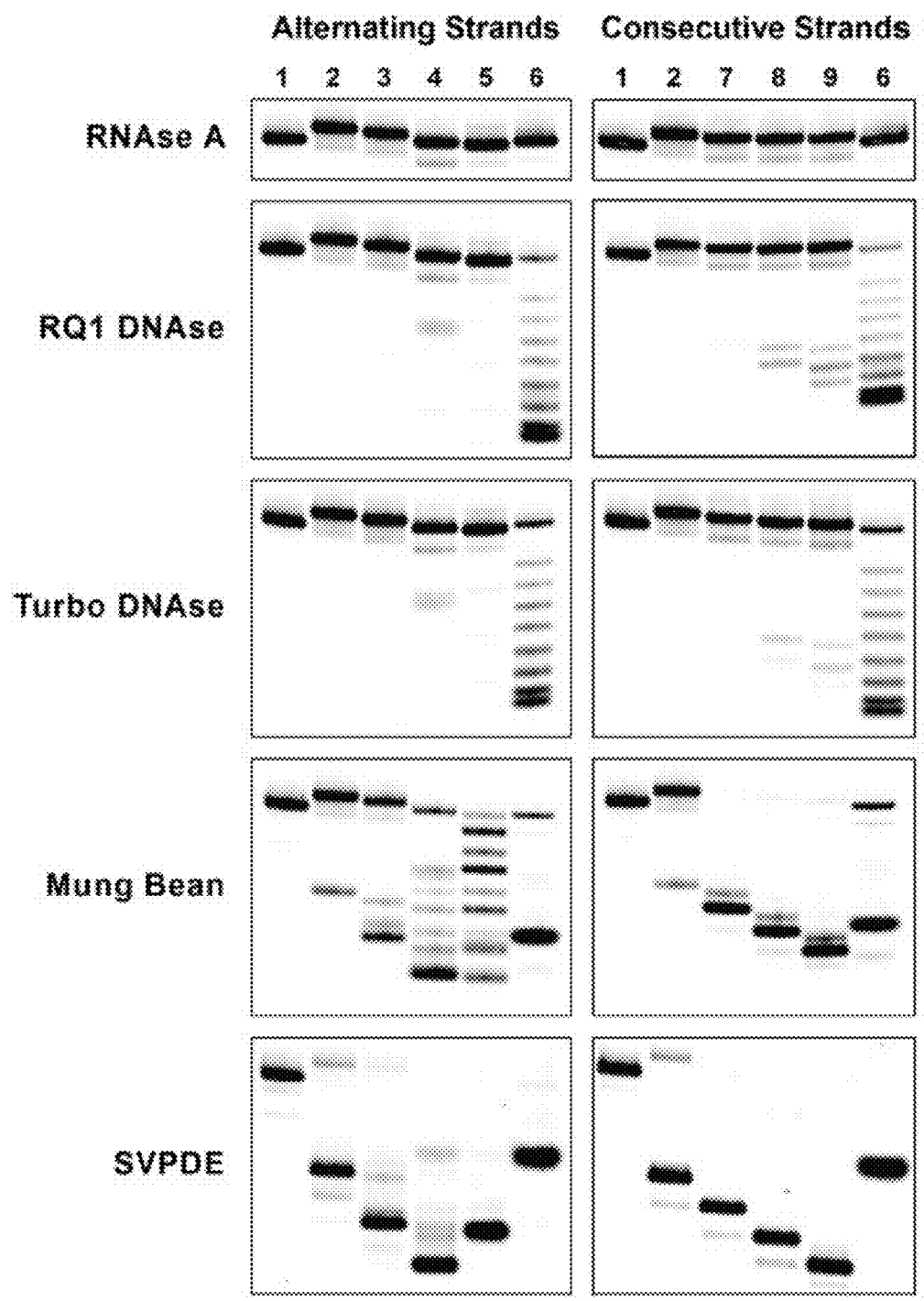
FIG. 4: Nuclease stability of TNA and mosaic TNA-DNA oligonucleotides. Oligonucleotide stability was evaluated by denaturing polyacrylamide gel electrophoresis following a 24-hour incubation at 37° C. Alternating and consecutive TNA-DNA sequences are provided in Tables 1 and 2.

We synthesized seven different mosaic TNA-DNA oligonucleotides that contain an increasing number of either alternating or consecutive DNA and TNA residues (SEQ. ID NOS: 2-5, and 7-10). In addition, the TNA and DNA strands generated for the pH stability study were used as controls for the all-TNA (SEQ ID. NOS: 1, and 11-13) and all-DNA (SEQ ID NO: 6) backbone structures. In each assay, the mosaic TNA-DNA strands along with the all-TNA and all-DNA controls were incubated with nuclease for 24 hours at 37° C. The samples were then treated with stop buffer and analyzed by denaturing polyacrylamide gel electrophoresis. Under these conditions, the all-TNA strand is completely stable against all of the enzymes tested, while the DNA control is digested by every nuclease except RNase A, which is highly specific for RNA (FIG. 4). Remarkably, the mosaic TNA-DNA strands are highly stabilized by the flanking TNA residues and show very little degradation after a 24-hour incubation in the presence of RNAse A, RQ1 DNAse, and Turbo DNAse. This result demonstrates that TNA can protect limited stretches of DNA from endogenous nucleases that are commonly found in biological fluids.

However, TNA protection does not extend to less common nucleases with stronger endolytic activity. Mung bean nuclease, which degrades single-stranded DNA and RNA and is commonly used to cut stem-loop structures, is able to digest mosaic TNA-DNA strands that contain two or more consecutive DNA residues (FIG. 4). This enzyme is less active with alternating patterns of DNA-TNA residues and shows only limited ability to cleave a single isolated DNA residue in an otherwise TNA backbone. By contrast, SVPE, which is an aggressive enzyme with strong 3' exonuclease activity, is able to digest all of the internal DNA residues after 24 hours. Enzymatic digestion of the mosaic strands by mung bean nuclease and SVPE produces a distinct pattern of undigested fragments (FIG. 4). We postulate based on their electrophoretic mobility difference and the fact that TNA is not recognized by SVPE that the undigested bands correspond to the Fam-labeled TNA portion of each mosaic DNA-TNA strand. This prediction is consistent with our earlier digestion of a chimeric TNA-DNA oligonucleotide.

Stability Analysis in Human Serum, Human Liver Microsomes (HLM)

The stability of the TNA, DNA and RNA and combinations thereof were tested in human serum (HS) and human liver microsomes (HLM) as described for rat serum and rat liver microsomes above. Oligonucleutides were synthesized as described above or were purchased. Specifically, DNA and RNA 16mers, 2'-OMe-RNA 17mer, and 2'-F-RNA 20mer were purchased from Integrated DNA technologies. FANA, 2'-OMe-RNA, and 2'-F-RNA 16mers were purchased from Glenn Research. DNA 12mer and TNA 12mers and 16mers were synthesized via solid-phase synthesis as described above. Oligo concentrations were measured by spectrophotometry and diluted to a working concentration of 50 ng/µL with an extinction coefficient (no FAM label): 158600 $M^{-1}cm^{-1}$ and an extinction coefficient (FAM label): 179600 $M^{-1}cm^{-1}$. Oligomers used can be found in Table 3.

TABLE 3

| Sequences |
|---|
| TNA |

| | | | | |
|---|---|---|---|---|
| 12 nt: 3'-FAM-TCT CTC TCT CTC-2' (SEQ ID NO: 1) | 20 µL | 335 µM | 26 mg |
| 16 nt: 3'-AAA ACC CAC ACC ACC A-2' (SEQ ID NO: 16) | 100 µL | 110 µM | 50 mg |
| 16 nt: 3'-AAA ACC CAC ACC ACC A-FAM-2' (SEQ ID NO: 16) | 50 µL | 950 µM | 240 mg |
| 16 nt: 3'-CAC TCG TAT GCA GTA G-FAM-2' (SEQ ID NO: 17) | 100 µL | 460 µM | 210 mg |

| TNA (black) and DNA (bold) |
|---|

| | | | |
|---|---|---|---|
| 12 nt: 3'-FAM-TTT TTC TCT TTT-2' (SEQ ID NO: 3) | 80 µL | 953 µM | 304 mg |
| 12 nt: 3'-FAM-TTT CTC TCT TTT-2' (SEQ ID NO: 18) | 300 µL | 181 µM | 21 mg |
| 12 nt: 3'-FAM-TCT CTC TCT CTC-3' (SEQ ID NO: 5) | 70 µL | 251 µM | 70 mg |

TABLE 3-continued

Sequences

| | | | |
|---|---|---|---|
| 12 nt: 3'-FAM-TTT TTT CCT TTT-2' (SEQ ID NO: 7) | 40 µL | 15 µM | 240 ng |
| 12 nt: 3'-FAM-TTT TTC CCT TTT-2' (SEQ ID NO: 8) | 110 µL | 122 µM | 55 mg |
| 12 nt: 3'-FAM-TTT TCC CCT TTT-2' (SEQ ID NO: 9) | 100 µL | 1054 µM | 420 mg |

DNA

| | | | |
|---|---|---|---|
| 12 nt: 5'-FAM-CCC CCC CCC CCC-3' (SEQ ID NO:6) | 100 µL | 178 µM | 70 mg |
| 16 nt: 5'-AAA ACC CAC ACC ACC A-3' (SEQ ID NO:19) | 90 µL | 840 µM | 360 mg |
| 16 nt: 5'-AAA ACC CAC ACC ACC A-FAM-3' (SEQ ID NO: 19) | 40 µL | 1040 µM | 200 mg |
| 16 nt: 5'-TGG TGG TGT GGG TTT T-FAM-3' (SEQ ID NO: 20) | 100 µL | 880 µM | 490 mg |

RNA

| | | | |
|---|---|---|---|
| 16 nt: 5'-AAA ACC CAC ACC ACC A-FAM-3' (SEQ ID NO: 21) | 100 µL | 540 µM | 300 mg |
| 16 nt: 5'-UGG UGG UGU UUU UUU U-FAM-3' (SEQ ID NO: 22) | 50 µL | 610 µM | 170 mg |

FANA

| | | | |
|---|---|---|---|
| 16 nt: 5'-AAA ACC CAC ACC ACC A-FAM-3' (SEQ ID NO: 23) | 50 µL | 1010 µM | 280 mg |

2'-fluoro-RNA

| | | | |
|---|---|---|---|
| 16 nt: 5'-AAA ACC CAC ACC ACC A-FAM-3' (SEQ ID NO: 24) | 50 µL | 600 µM | 160 mg |
| 20 nt: 5'-GAC ACT CGT ATG CAG TAG CC-FAM-3' (SEQ ID NO: 25) | 50 µL | 150 µM | 50 mg |

2'-methoxy-RNA

| | | | |
|---|---|---|---|
| 16 nt: 5'-AAA ACC CAC ACC ACC A-FAM-3' (SEQ ID NO: 26) | 50 µL | 600 µM | 170 mg |
| 17 nt: 5'-GGA CCG GAA GGU ACG AG-FAM-3' (SEQ ID NO: 27) | 100 µL | 480 µM | 300 mg |

Master mixes of reactions prepared with 50 ng of labeled oligonucleotide, at 10 µM, and divided into 10 µL aliquots in separate tubes (final concentration 1 µM, 10 µL reaction volume) and added to either human serum (HS) or human liver microsomes (HLM). Human serum conditions were 50% human serum (Sgima-Aldrich) and 50% DMEM media (ThermoFisher). Human liver microsomes conditions were 0.5 mg/mL HLM (Xenotech), HLM buffer: 10 mM Tris-HCl, 0.1 mM MgCl2, pH 8.0. Controls were prepared containing only oligonucleotide in buffer. Mixtures were incubated at 37° C. in the dark. The reactions were stopped at specific time points by adding 10 µL stop buffer (8 M urea, 5 mM Tris-HCl, 20 mM EDTA, pH 7.5) and heating for 5 min at 90° C. 5 µL loading dye (50% glycerol, 50 mM Tris, 50 mM EDTA, xylene cyanol, bromothymol blue) was added to samples and analyzed by 20% denaturing PAGE.

Figure 8:
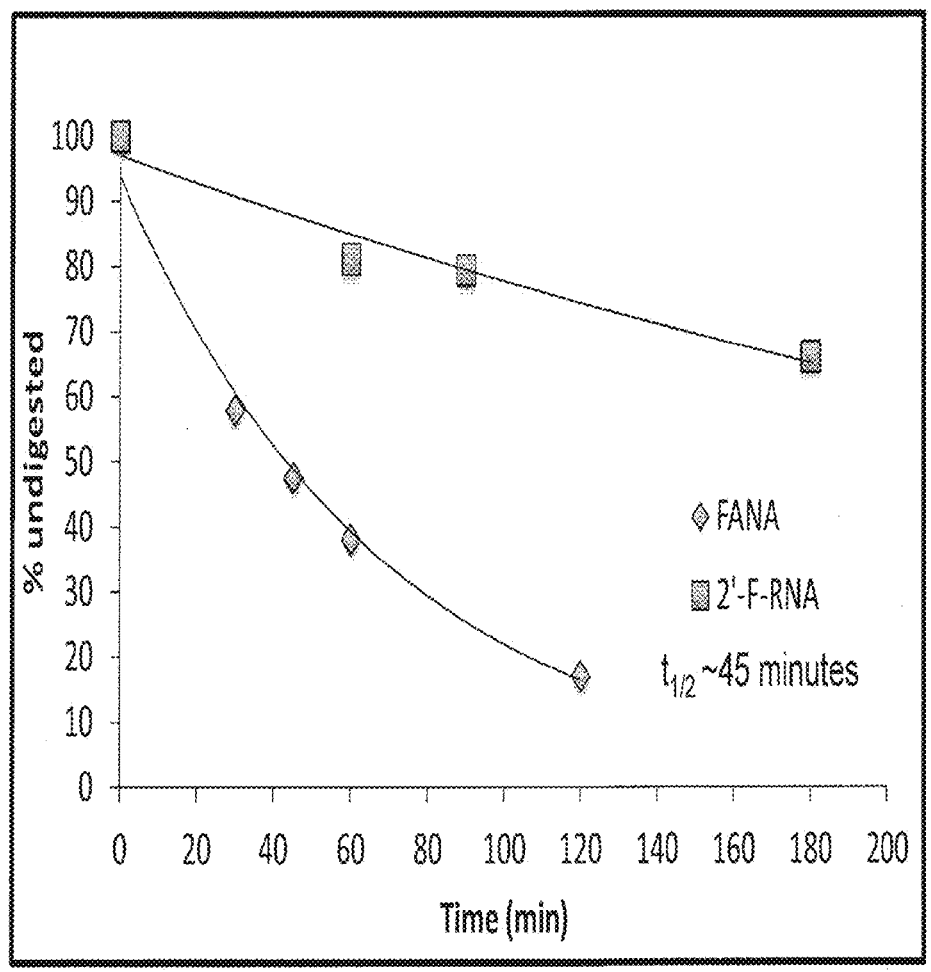
FIG. 8 is a graph depicting the % undigested FANA or 2'-F-RNA over time in human serum solution at 37° C.
Figure 9:
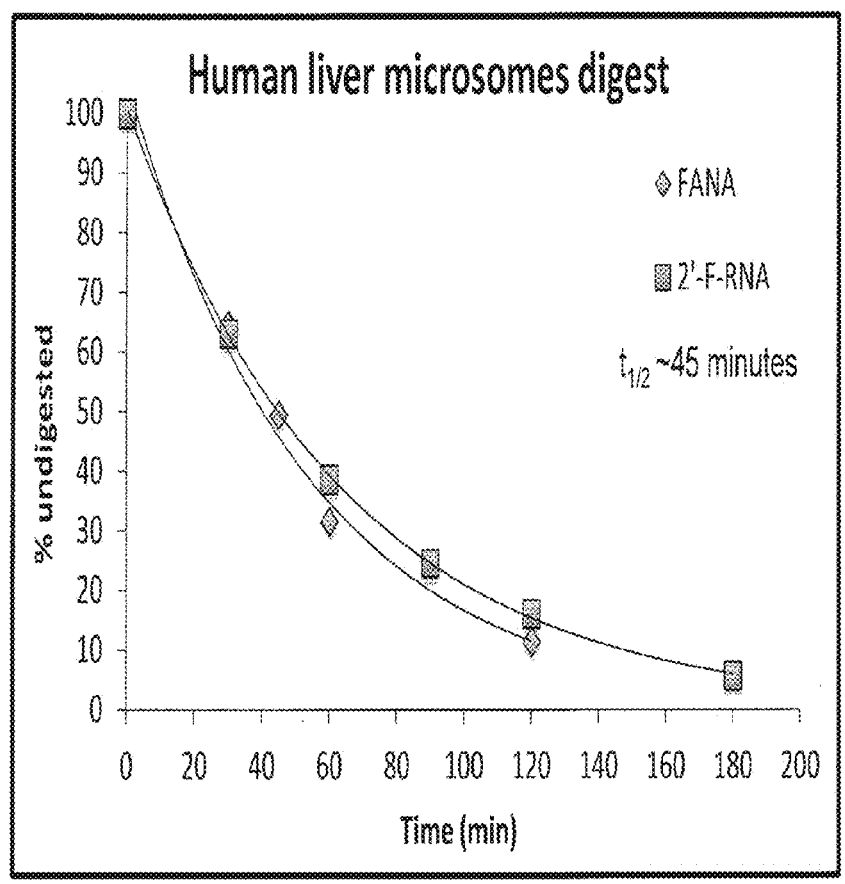
FIG. 9 is a graph depicting the % undigested FANA or 2'-F-RNA over time in human liver microsome solution at 37° C.
Figure 10:
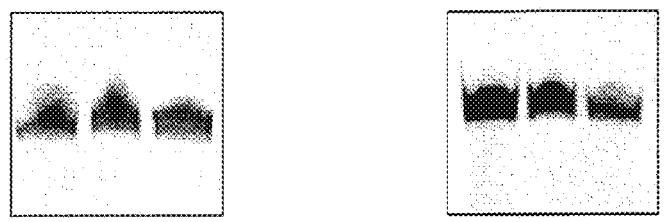
FIG. 10 contains images depicting TNA stability is not sequence specific by showing two different sequences digested in buffer (1), human serum (2) or human liver microsomes (3) for 7 days at 37° C.

FANA and 2'-F-RNA consistently digest in human serum (HS, see FIG. 8) and human liver microsomes (HLM, see FIG. 9) with $t_{1/2}$<3 hours. TNA does not degrade after 7 days in both HS and HLM, independent of sequence as demonstrated in FIG. 10.

Duplex Stability Study

Figure 11:
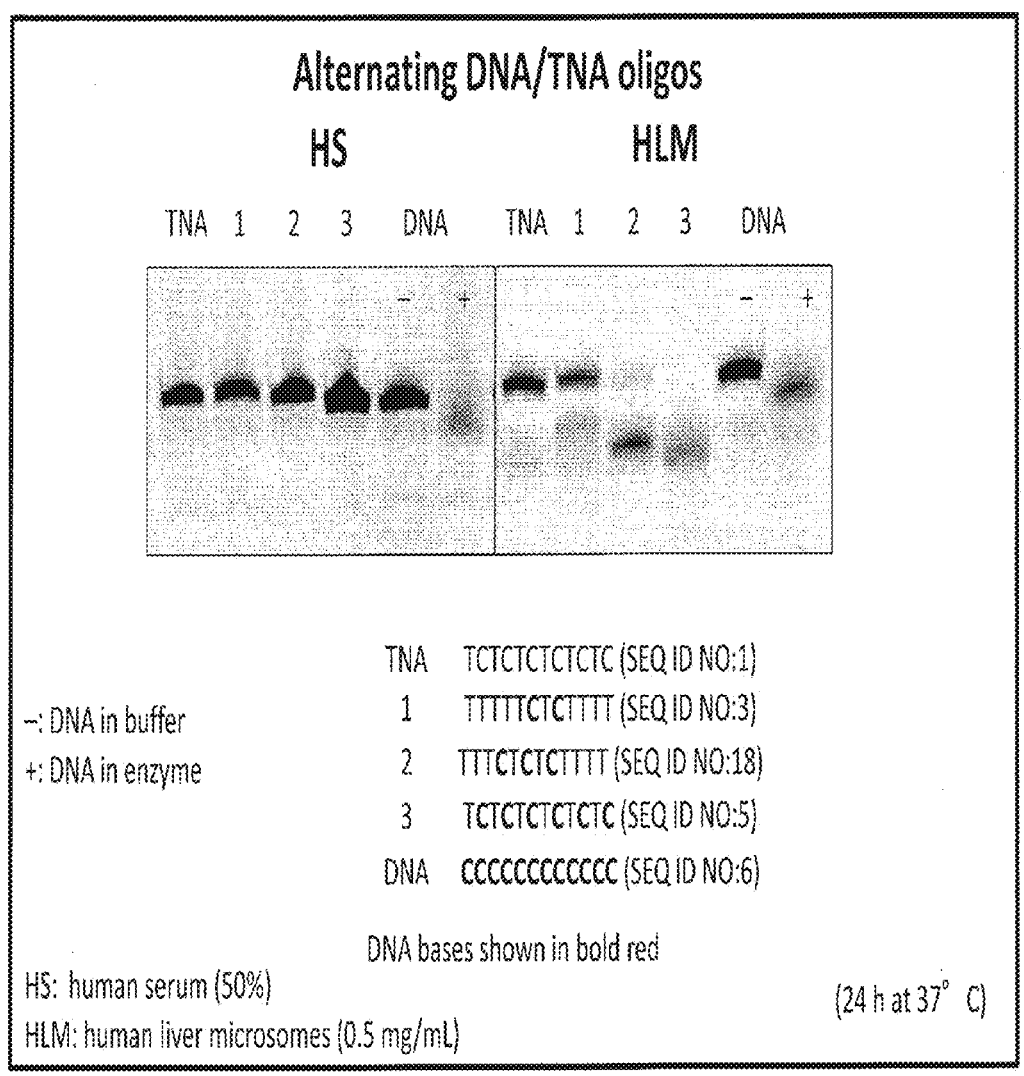
FIG. 11 contains image of a gel demonstrating that TNA has protective effect on DNA/TNA oligomers. TNA, or sequences containing DNA/TNA oligomers ((1), (2), and (3)) were incubated with either human serum (HS) or human liver microsomes (HLM) for 24 hours at 37° C. Control shows DNA either in buffer alone (negative control) or added enzyme (positive control).
Figure 12:
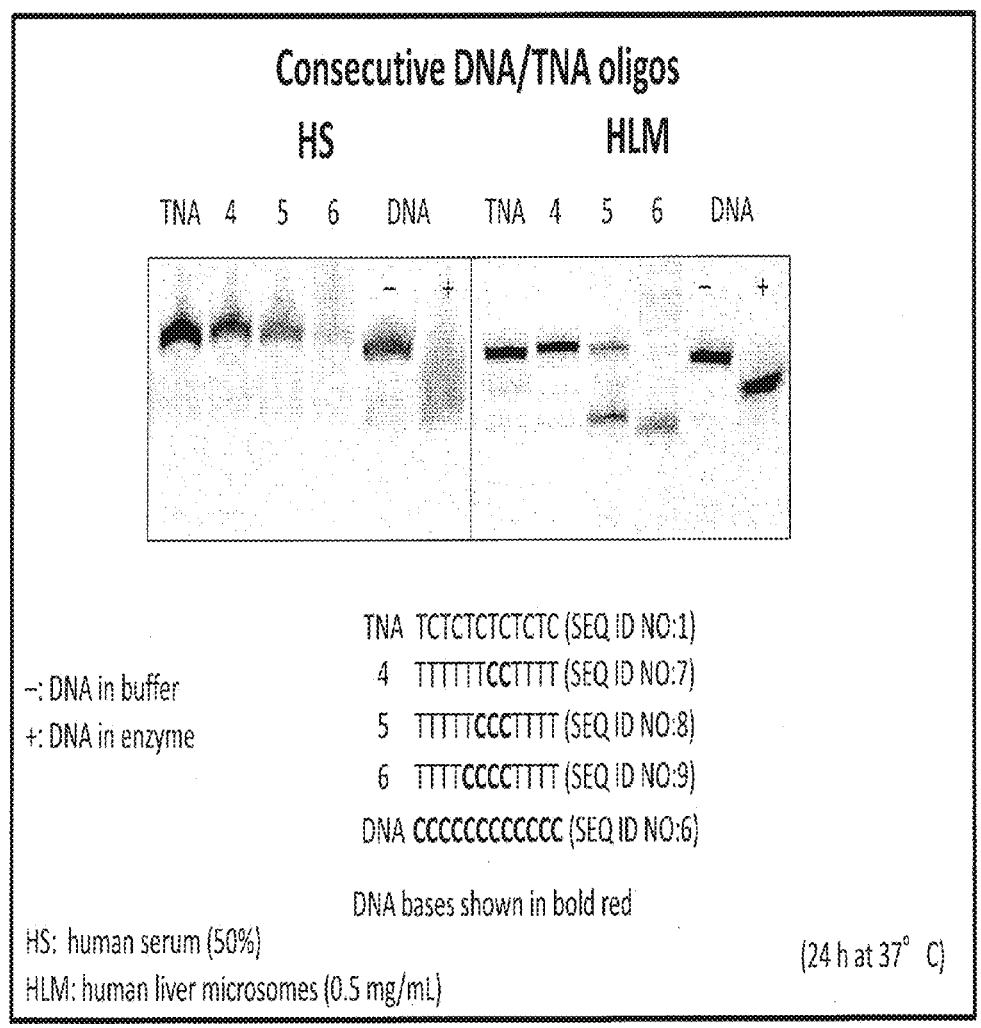
FIG. 12 contains image of a gel demonstrating that TNA has protective effect on DNA/TNA oligomers. TNA, or sequences containing DNA/TNA oligomers ((4), (5), and (6)) were incubated with either human serum (HS) or human liver microsomes (HLM) for 24 hours at 37° C. Control shows DNA either in buffer alone (negative control) or added enzyme (positive control).
Figure 13:
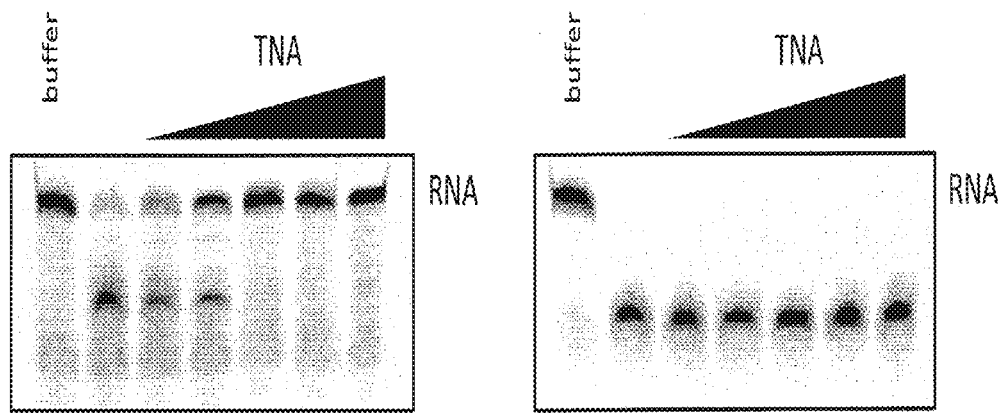
FIG. 13 contain images of gels demonstrating TNA has a protective effect on RNA. Increasing amounts of TNA complementary to the RNA (left) or non-complementary to the RNA (right) was incubated with RNA in the presence of human liver microsomes for 10 minutes at 37° C. Samples were run on a 20% denaturing PAGE. RNA in buffer alone was run as a positive control.
Figure 14:
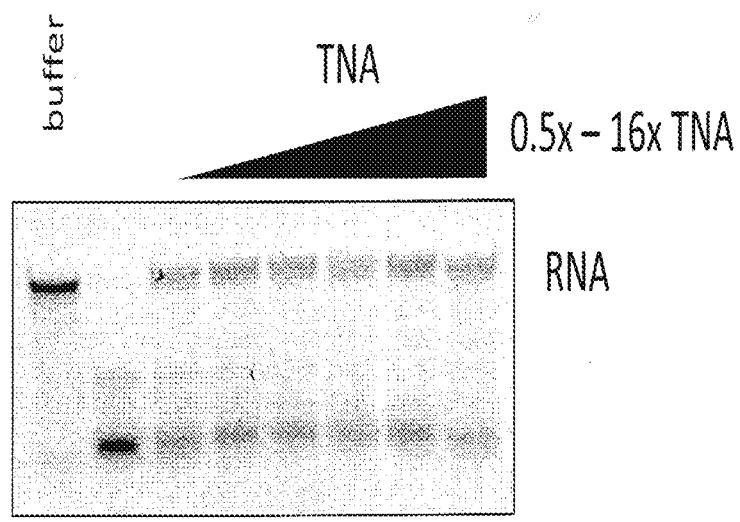
FIG. 14 is an image of a gel demonstrating TNA has a protective effect on RNA. Increasing amounts TNA complementary to RNA was added to RNA in HLM solution and incubated for 3 hours at 37° C. Samples were run on a gel and imaged.

Duplex stability was tested using the oligomers of Table 3. The annealing reaction contained 75 ng RNA, and 375 ng TNA or DNA in 4.5 µL water. Control samples were prepared with only 75 ng RNA in water. Master mix was prepared and then heated at 70° C. for 2 min, followed by addition of 0.5 µL magnesium buffer (20 mM Tris, 100 mM NaCl, 5 mM Mg, pH 8.0). Samples cooled on ice for at least 2 min, Reactions were carried out either in Human Serum or human liver microsomes. In HS reaction, HS was added to final concentration of 50% in 10 µL reaction. In the HLM reaction, HLM added to final concentration of 0.5 mg/mL in 10 µL reaction. Reaction tubes were incubated at 37° C. in the dark. The reactions were stopped at specific time points by adding 10 µL stop buffer (8 M urea, 5 mM Tris-HCl, 20 mM EDTA, pH 7.5) and heating for 5 min at 90° C. 5 µL loading dye (50% glycerol, 50 mM Tris, 50 mM EDTA, xylene cyanol, bromothymol blue) was added to samples and analyzed by 20% denaturing PAGE. Results are shown in FIGS. 11-14. TNA can protect DNA from enzymatic digestion in TNA-DNA heteropolymers (FIG. 11 and FIG. 12). TNA can protect RNA when annealed in TNA-RNA duplexes (FIG. 13 and FIG. 14).

Discussion.

Functional nucleic acid molecules isolated by in vitro selection are currently being developed for use as diagnostics, therapeutics, and biosensors, as well as for new tools in chemical biology[6-8, 28-31]. Aptamers, single-stranded molecules that fold into shapes with ligand binding affinity, can be thought of as 'chemical antibodies' as they exhibit high target binding affinity, but are generated by chemical synthesis rather than cell culture[32]. Chemical synthesis provides a straightforward and cost-effective approach for producing large quantities of affinity reagents using methods that avoid viral or bacterial contaminants. Compared to antibodies, aptamers exhibit low immunogenicity, undergo reversible folding, and have functions that can be tailored to specific applications by directed evolution[6]. However, despite these advantages, aptamers are susceptible to nuclease degradation, and early studies showed that unmodified aptamers have a half-life of just a few minutes in biological environments, such as human serum[33,34].

Recognizing that bioavailability is a significant barrier to the development of nucleic acid molecules for clinical applications, chemists have synthesized hundreds of DNA and RNA analogues that retain the ability to bind RNA, but are more stable to biological environments[35]. Chemically modified sugars, in particular, have shown great promise as nucleic acid analogues that can stabilize the backbone structure against nucleases[36].

Popular substitutions include 2'-OMe, 2'-F, and 2'-methoxyethyl derivatives as well as more diverse structures like 2'-deoxy-2-fluoro-β-D-arabino nucleic acid (2'F-ANA) and the 2' methylene bridged analogue known as locked nucleic acid (LNA). Some of these modifications are found in the FDA-approved drugs Macugen and Kynamro due to their nuclease stability and affinity for RNA[37,38].

While chemical modifications can impart nuclease resistance activity on natural genetic polymers, the emerging field of synthetic genetics aims to develop artificial genetic polymers that are invisible to biological enzymes[12]. In the current study, we show that TNA is completely stable against all of the nucleases tested, including SVPE, which has strong hydrolytic activity. We also show that TNA remains undigested after 24 hours of incubation in the presence of mouse serum and rat lysosomal lysate—two in vitro conditions used that strongly correlate with oligonucleotide stability in vivo[27]. Additional data shows that TNA is completely resistant to nuclease degradation. In fact, we have yet to find an enzyme that will degrade TNA after 72 hours.

These observations suggest that TNA may be one of the most nuclease resistant analogues developed to date. By comparison, 2'-F-RNA and FANA degrade in minutes when incubated in the presence of SVPE, while 2'-OMe RNA is more stable and degrades over a period of hours[39,40]. LNA is reported to be completely stable to SVPE; however, the only known study was limited to a two-hour incubation, which is insufficient to provide a complete biostability profile[41].

We now show that backbone structure has a dramatic effect on nuclease stability. For example, we show that TNA, which contains 2'-3' phosphodiester linkages, is completely stable to nuclease digestion, while the 3'-5' linkages found in DNA and RNA are rapidly degraded. Mosaic TNA-DNA strands, which contain 2'-5' phosphodiester linkages at their TNA-DNA junctions, the same linkages found in natural 2'-5' polyadenylated DNA, have intermediate stability.

We can therefore now potentially design TNA molecules that function with programmed half-lives in biological systems by engineering alternative linkages into the backbone structure or by selecting for functional TNA-DNA heteropolymers with mosaic backbone structures. This property may be used in the development of therapeutic and drug-delivery applications, where it is advantageous for the TNA strand to degrade once it has reached its cellular target.

Further, the stable, nuclease-resistant TNA oligonucleotide of the present invention may be used as a therapeutic (antisense, catalyst, RNAi, etc.), affinity reagent (aptamer, ribozyme) for diagnostic drug delivery, diagnostic testing, imaging ad the like. In one embodiment, the stable, nuclease-resistant TNA oligonucleotide could be substituted in part or in whole for any application that currently uses DNA or RNA.

In the context of chemical stability, we found that TNA behaves similar to DNA in extreme acidic and alkaline environments. Under these conditions, RNA is rapidly degraded due to acid and base-catalyzed attack of the 2' hydroxyl group on the phosphodiester bond. However, DNA and TNA, which lack a 2' hydroxyl moiety, are both stable after 3 days in simulated gastric fluid, but degrade with slightly different half lives under high alkaline conditions. In 1 M NaOH at 65° C., DNA was found to be less stable than TNA (half-life of 1.5 vs. 6 hours, respectively). The enhanced alkaline stability of TNA relative to DNA could be due to the absence of a 5' carbon atom, which makes TNA a more compact structure that is less accessible to nucleophilic attack by free hydroxyl groups. This level of chemical stability could be useful in non-biological applications, such as nanotechnology, where enhanced chemical stability is necessary for oligonucleotide assembly and function.

In summary, we find that the TNA and TNA-DNA oligonucleotides of the present invention are biologically stable nucleic acid polymers that are highly resistant to enzymes that degrade DNA and RNA. In addition to the development of aptamers and catalysts, the enhanced nuclease resistant properties of the TNA and TNA-DNA oligonucleotides of the present invention could be practically applied in a wide range of therapeutic nucleic acid technologies that include antisense, siRNA, and anti-microRNA, as well as new engineering materials for chemical biology and nanotechnology.

The above description, attached figures, and claims listed below are intended to be illustrative and not limiting of this invention. In light of the invention described herein, many themes and variations to this invention will be suggested to one skilled in the art. All such themes and variations are within the contemplation hereof. For instance, while this invention has been described in conjunction with the various exemplary embodiments outlined above and in the below claims, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. A stable, nuclease-resistant TNA-DNA oligonucleotide, wherein the TNA-DNA oligonucleotide comprises an effective amount of TNA to provide resistance to enzymatic degradation in a biological environment wherein at least half of the nucleotides are TNA.

2. The nuclease-resistant TNA-DNA oligonucleotide of claim 1, wherein the effective amount of TNA comprises at least two TNA nucleic acids.

3. The nuclease-resistant TNA-DNA oligonucleotide of claim 1, wherein the effective amount of TNA comprises at least three TNA nucleic acids.

4. A method of preparing a nuclease-resistant TNA-DNA oligonucleotide of claim 1, the method comprising inserting an effective amount of TNA into a sample of DNA to yield a TNA-DNA oligonucleotide, wherein the TNA-DNA oligonucleotide is resistant to enzymatic degradation in a biological environment.

5. The method of claim 4, wherein the TNA-DNA oligonucleotide is resistant to enzyme degradation for at least 24 hours.

6. The method of claim 4, wherein the effective amount of TNA comprises more than one nucleic acid of TNA.

7. The method of claim 4, wherein the TNA residues alternate with DNA residues.

8. The method of claim 4, wherein the TNA residues comprise at least half of the TNA-DNA oligonucleotide.

9. The method of claim 4, wherein the TNA-DNA oligonucleotide is resistant to enzyme degradation for at least 72 hours.

10. The nuclease-resistant DNA-TNA oligonucleotide of claim 1, wherein the TNA residues alternate with DNA residues within the oligonucleotide.

11. The nuclease-resistant DNA-TNA oligonucleotide of claim 1, wherein the biological environment is blood, biological fluid or serum.

12. The method of claim 4, wherein the biological environment is blood, biological fluid or serum.

* * * * *